(12) United States Patent
Shaw et al.

(10) Patent No.: US 12,285,631 B2
(45) Date of Patent: *Apr. 29, 2025

(54) ADJUSTABLE MULTI-SLIT COLLIMATORS

(71) Applicant: UNM Rainforest Innovations, Albuquerque, NM (US)

(72) Inventors: Richard Shaw, Albuquerque, NM (US); Shuang Luan, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/313,704

(22) Filed: May 8, 2023

(65) Prior Publication Data

US 2023/0347178 A1    Nov. 2, 2023

Related U.S. Application Data

(63) Continuation of application No. 17/229,775, filed on Apr. 13, 2021, now Pat. No. 11,679,277.

(60) Provisional application No. 63/009,280, filed on Apr. 13, 2020.

(51) Int. Cl.
*A61N 5/10*    (2006.01)

(52) U.S. Cl.
CPC ......... *A61N 5/1045* (2013.01); *A61N 5/1081* (2013.01)

(58) Field of Classification Search
None
See application file for complete search history.

(56) References Cited

U.S. PATENT DOCUMENTS

| | | | |
|---|---|---|---|
| 8,295,436 B2 | 10/2012 | Nord et al. | |
| 9,138,598 B2 | 9/2015 | Nord et al. | |
| RE46,953 E | 7/2018 | Yu et al. | |
| 11,679,277 B2 * | 6/2023 | Shaw | A61N 5/1045 378/65 |
| 2004/0034269 A1 | 2/2004 | Ozaki | |
| 2010/0006778 A1 | 1/2010 | Flynn et al. | |
| 2010/0243921 A1 | 9/2010 | Flynn et al. | |
| 2010/0270480 A1 * | 10/2010 | Echner | A61N 5/1042 250/492.1 |
| 2011/0051893 A1 | 3/2011 | Mcnutt et al. | |

(Continued)

OTHER PUBLICATIONS

"U.S. Appl. No. 17/229,775, Non Final Office Action filed Sep. 15, 2022", 10 pgs.

(Continued)

*Primary Examiner* — Marcus H Taningco
(74) *Attorney, Agent, or Firm* — Schwegman Lundberg & Woessner, P.A.

(57) ABSTRACT

The transverse intensity distribution of a beam of x-rays or other radiation can be modulated with a multi-slit collimator device that includes one or more sets of collimator leaves arranged in a one-dimensional array and individually movable to form slits of variable width between pairs of adjacent collimator leaves. A two-dimensional intensity distribution may be achieved using multiple sets of one-dimensionally arranged leaves, e.g., by stacking them along the beam in different orientations, or by stacking them in a transverse direction to form a two-dimensional array of leaves. In some embodiments, the multi-slit collimator device also serves beam-monitoring purposes.

20 Claims, 22 Drawing Sheets

(56) References Cited

U.S. PATENT DOCUMENTS

| | | |
|---|---|---|
| 2012/0256103 A1 | 10/2012 | Luzzara |
| 2013/0023718 A1 | 1/2013 | Nord et al. |
| 2013/0077751 A1 | 3/2013 | Gunawardena et al. |
| 2015/0170778 A1 | 6/2015 | Echner et al. |
| 2017/0143995 A1 | 5/2017 | Bergfjord |
| 2017/0157423 A1 | 6/2017 | Bokrantz et al. |
| 2020/0206535 A1 | 7/2020 | Rieger et al. |
| 2020/0238106 A1 | 7/2020 | Xiao et al. |
| 2021/0316158 A1 | 10/2021 | Shaw et al. |

OTHER PUBLICATIONS

"U.S. Appl. No. 17/229,775, Notice of Allowance filed Feb. 8, 2023", 8 pgs.

"U.S. Appl. No. 17/229,775, Response filed Dec. 15, 2022 to Non Final Office Action filed Sep. 15, 2022", 7 pgs.

* cited by examiner

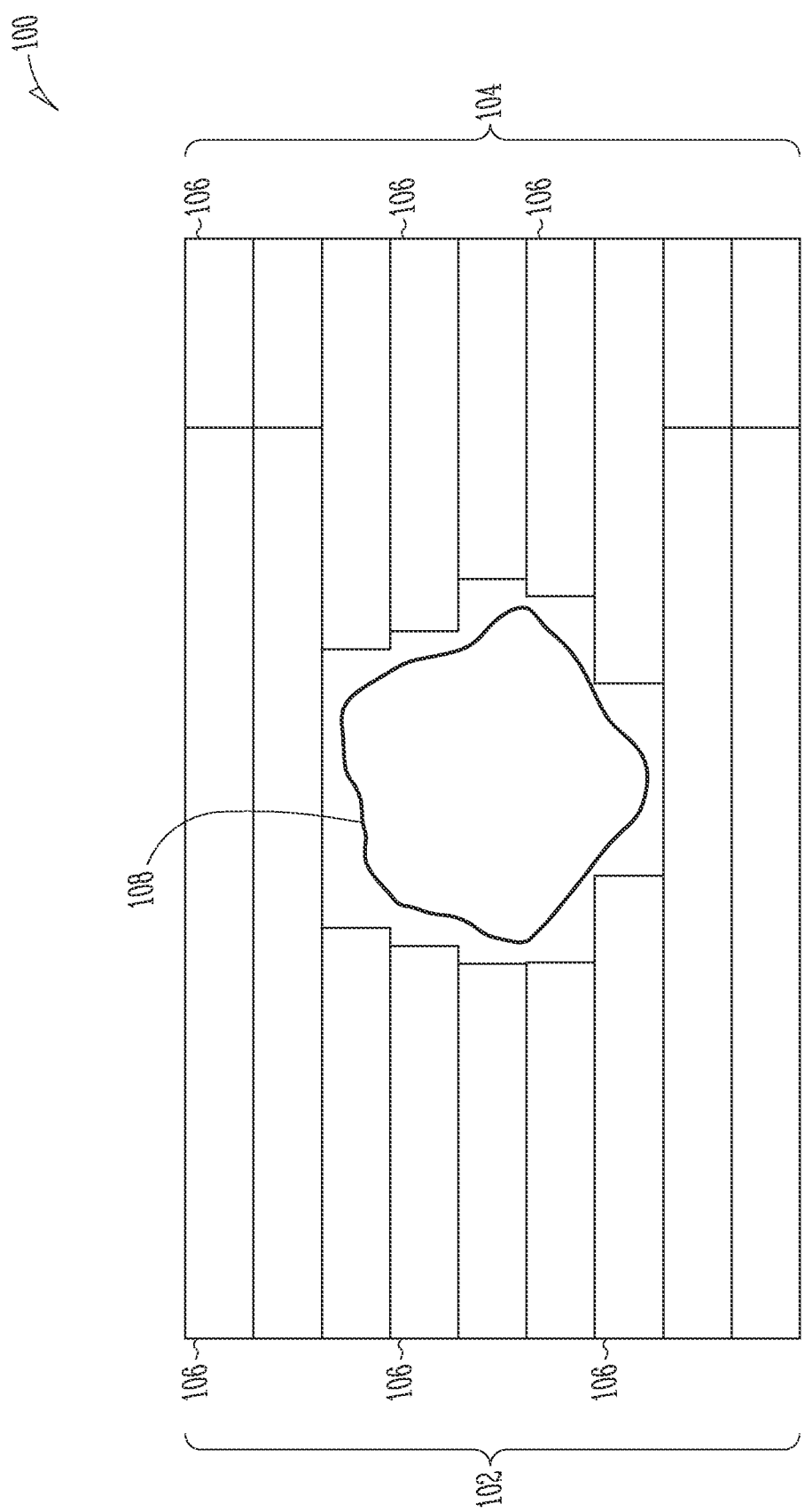

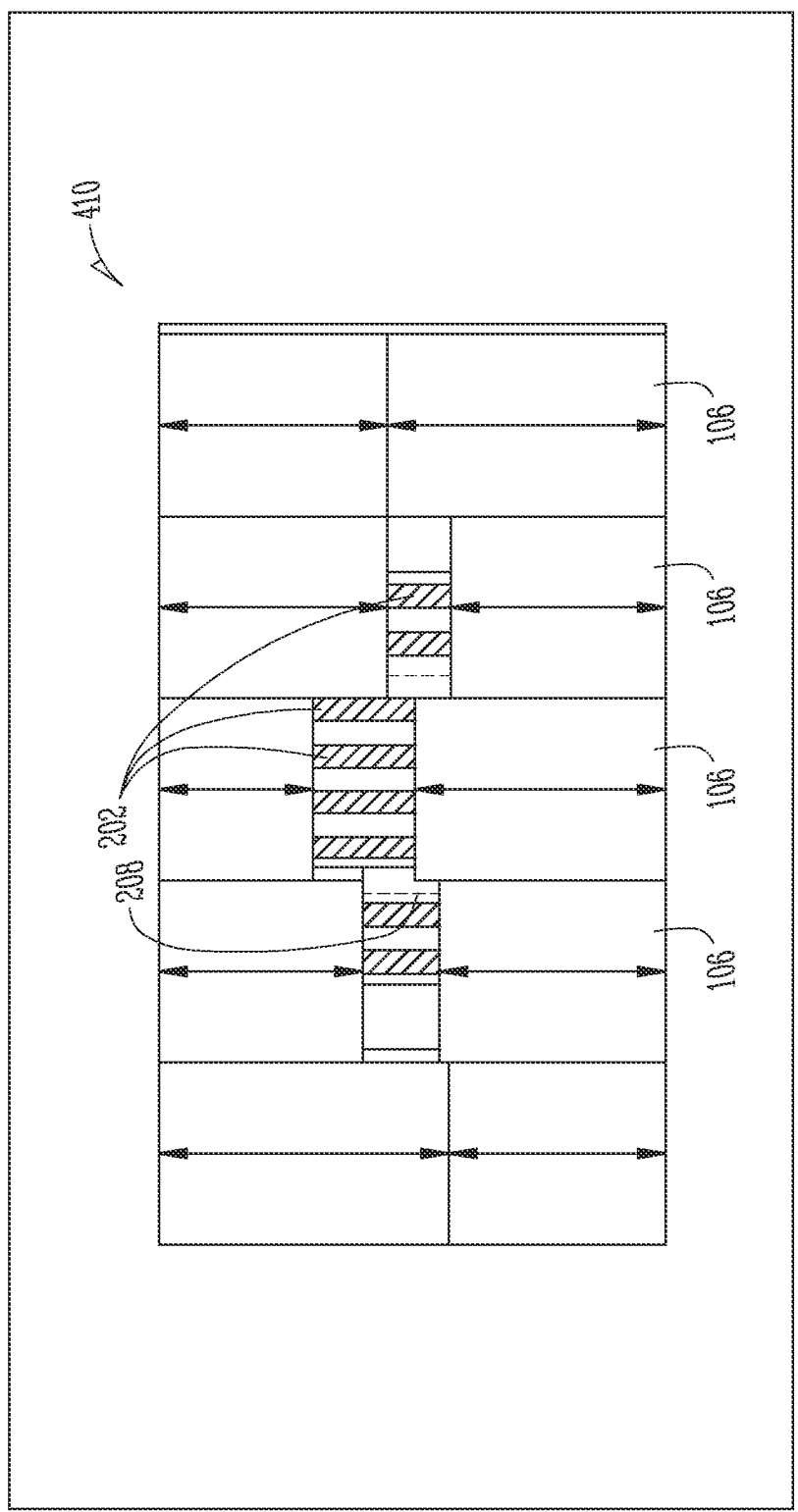
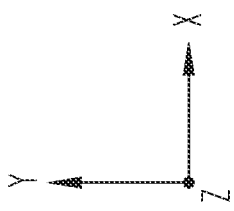
Fig. 4B

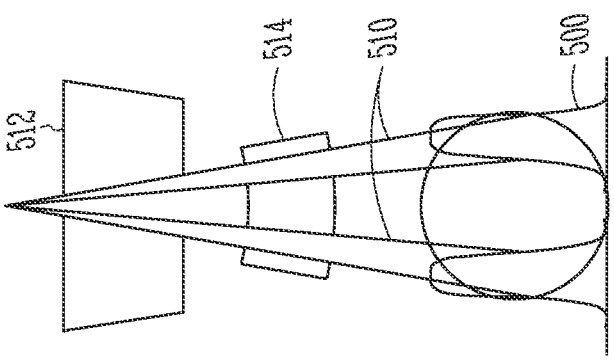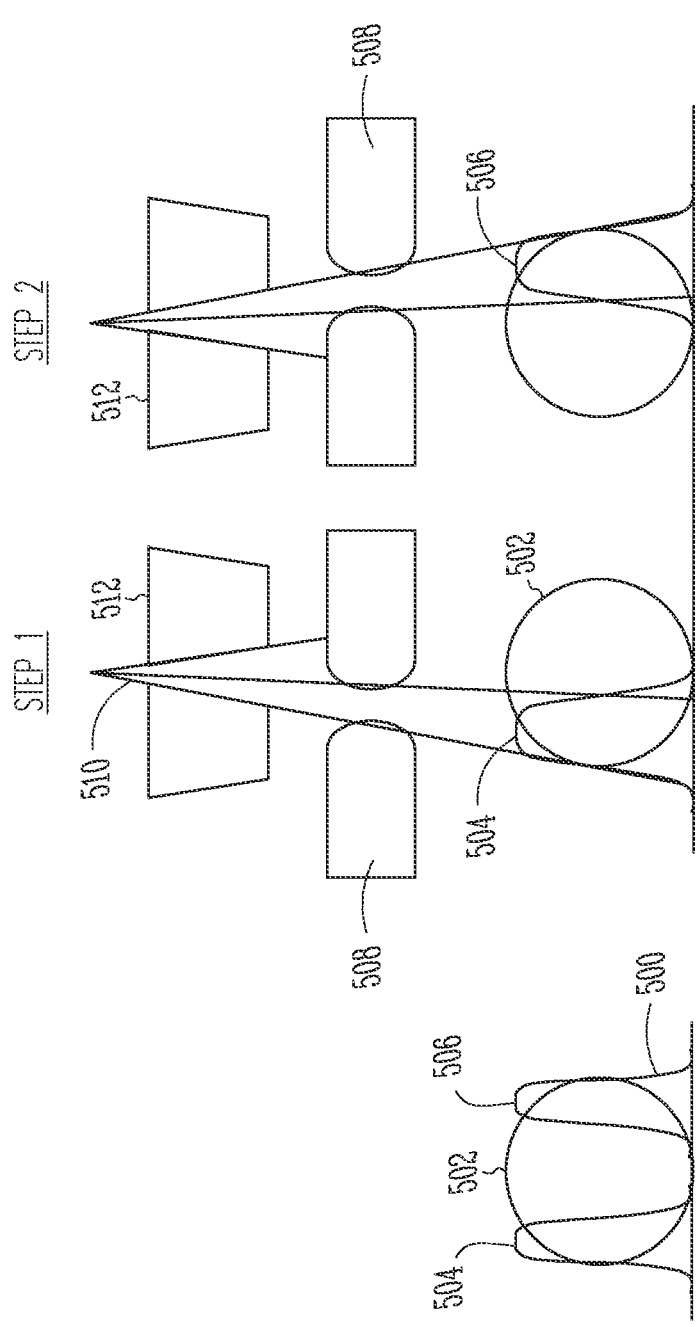
Fig. 5A  Fig. 5B  Fig. 5C

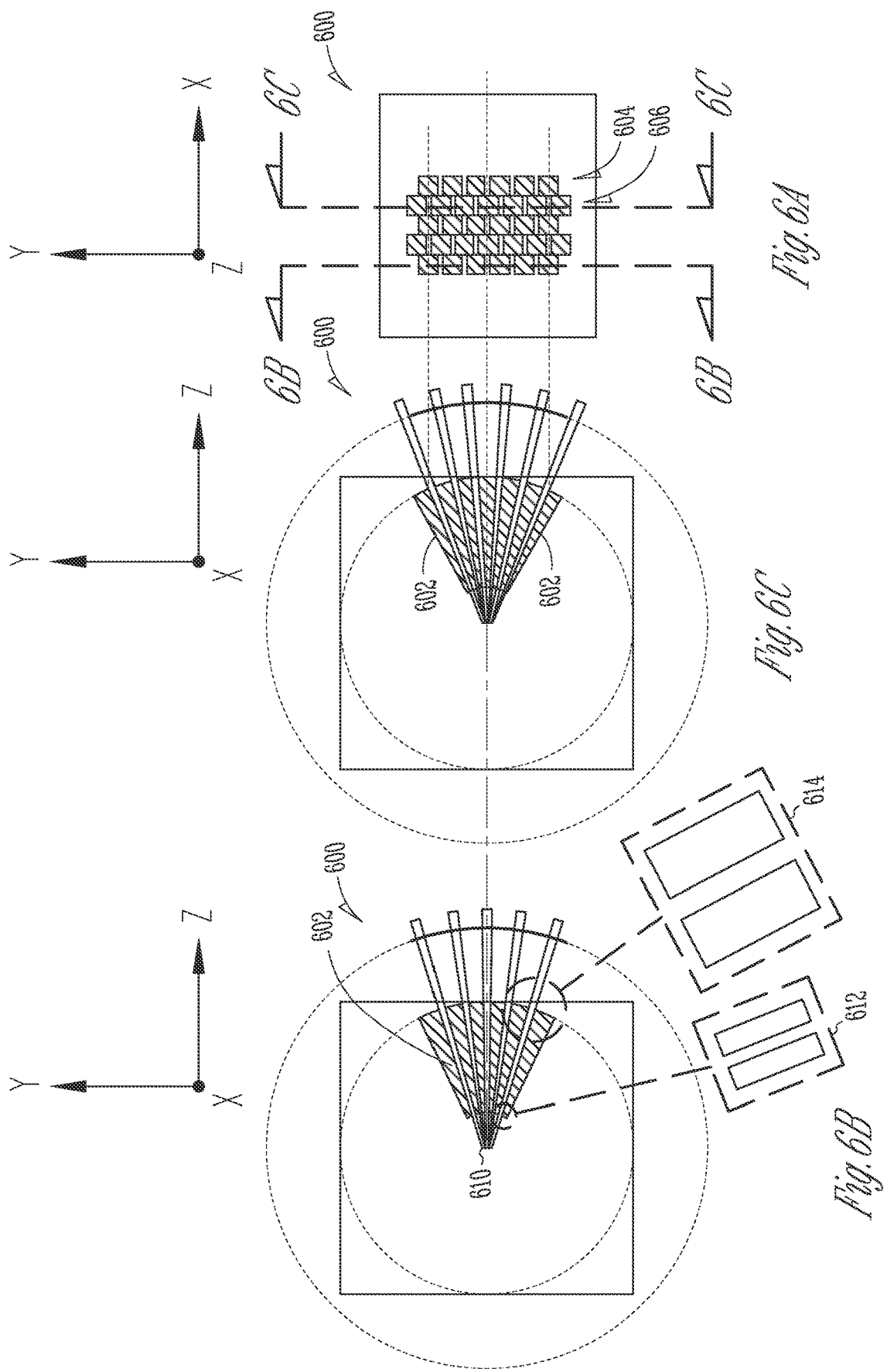

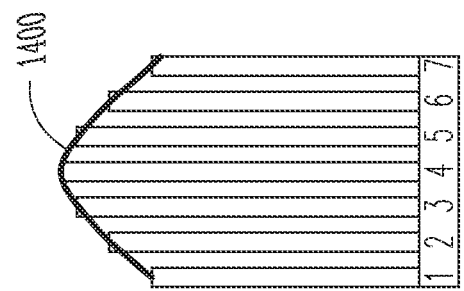
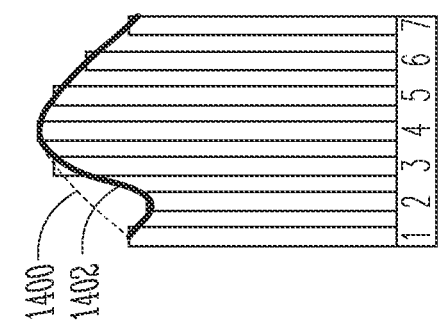
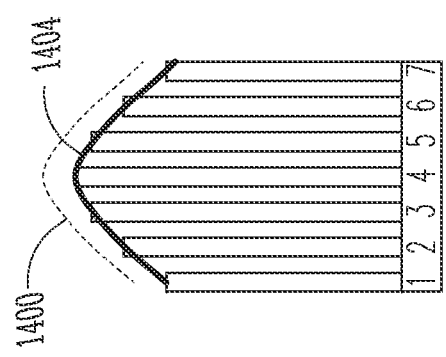
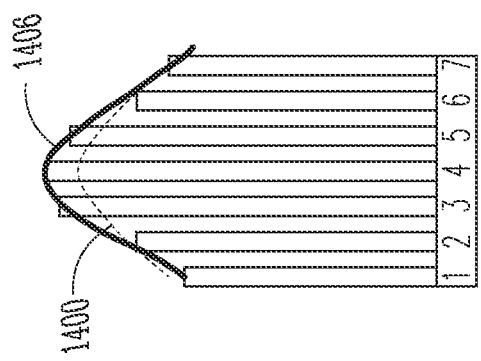

ADJUSTABLE MULTI-SLIT COLLIMATORS

CROSS-REFERENCE TO RELATED APPLICATION

This application is a continuation of U.S. patent application Ser. No. 17/229,775, filed Apr. 13, 2021, which application claims priority to U.S. Provisional Patent Application No. 63/009,280, filed on Apr. 13, 2020, which is hereby incorporated herein by reference in its entirety.

TECHNICAL FIELD

This disclosure relates to collimators for use in radiation therapy.

BACKGROUND

Radiation therapy has long been used to shrink and/or kill cancerous tissue through exposure to high doses of high-energy radiation. A device commonly employed in radiation therapy is a linear accelerator (LINAC), which accelerates charged particles, such as protons, electrons, or ions, to high energies, and uses them either directly as the therapeutic beam, or converts them to other forms of radiation. In x-ray therapy, for instance, a high-energy (e.g., 6 MeV) electron beam generated in the LINAC may be directed onto an x-ray converter target, such as a sheet of tungsten or another heavy metal, to create, via interactions of the electrons with the target, x-rays with energies up to the energy of the incident electrons. The LINAC may be mounted within a gantry that can be rotated around a patient to allow irradiating the treatment target, such as a tumor, from different angles to thereby accumulate absorbed radiation doses primarily within the treatment target. To optimize the conformity of the delivered dose to the treatment target and thereby maximize treatment efficacy while minimizing damage to healthy tissue, the intensity of the therapeutic (e.g., x-ray) beam and/or the beam shape may be varied as a function of the angle from which the beam is directed onto the treatment target, e.g., in techniques such as intensity-modulated radiation therapy (IMRT) or volumetric modulated arc therapy (VMAT). Intensity modulation can be achieved by operating the LINAC to produce more or less radiation, while the beam shape can be adjusted, e.g., using a multi-leaf collimator (MLC) placed in the therapeutic beam between the source of the beam and the treatment target.

BRIEF DESCRIPTION OF THE DRAWINGS

The subject matter of this disclosure will be described with reference to the accompanying drawings, in which:

FIG. 1 schematically depicts an example MLC in beam's eye view;

FIGS. 4A and 4B depict, in beam's eye view, an adjustable MSC by itself and the MSC in conjunction with a perpendicularly oriented conventional MLC, respectively, in accordance with one embodiment;

FIG. 5A depicts an example desired radiation dose distribution relative to a spherical target;

FIG. 5B illustrates two steps of creating the desired dose distribution of FIG. 5A with an MLC used sequentially in two different transverse positions;

FIG. 5C illustrates a two-slit configuration of an MSC, in accordance with one embodiment, that achieves the desired dose distribution of FIG. 5A in a single step;

FIG. 6A depicts, in beam's eye view, an example two-dimensional arrangement of collimator leaves of an adjustable MSC in accordance with one embodiment;

FIGS. 6B and 6C are cross-sectional views of the example two-dimensional collimator leaf arrangement of FIG. 6A along two planes, illustrating the leaf configuration and orientation relative to a radiation source;

FIGS. 14A-14D illustrate example detector response curves obtained with an MSC as shown in FIG. 13, in accordance with various embodiments.

DESCRIPTION

Figure 2A:
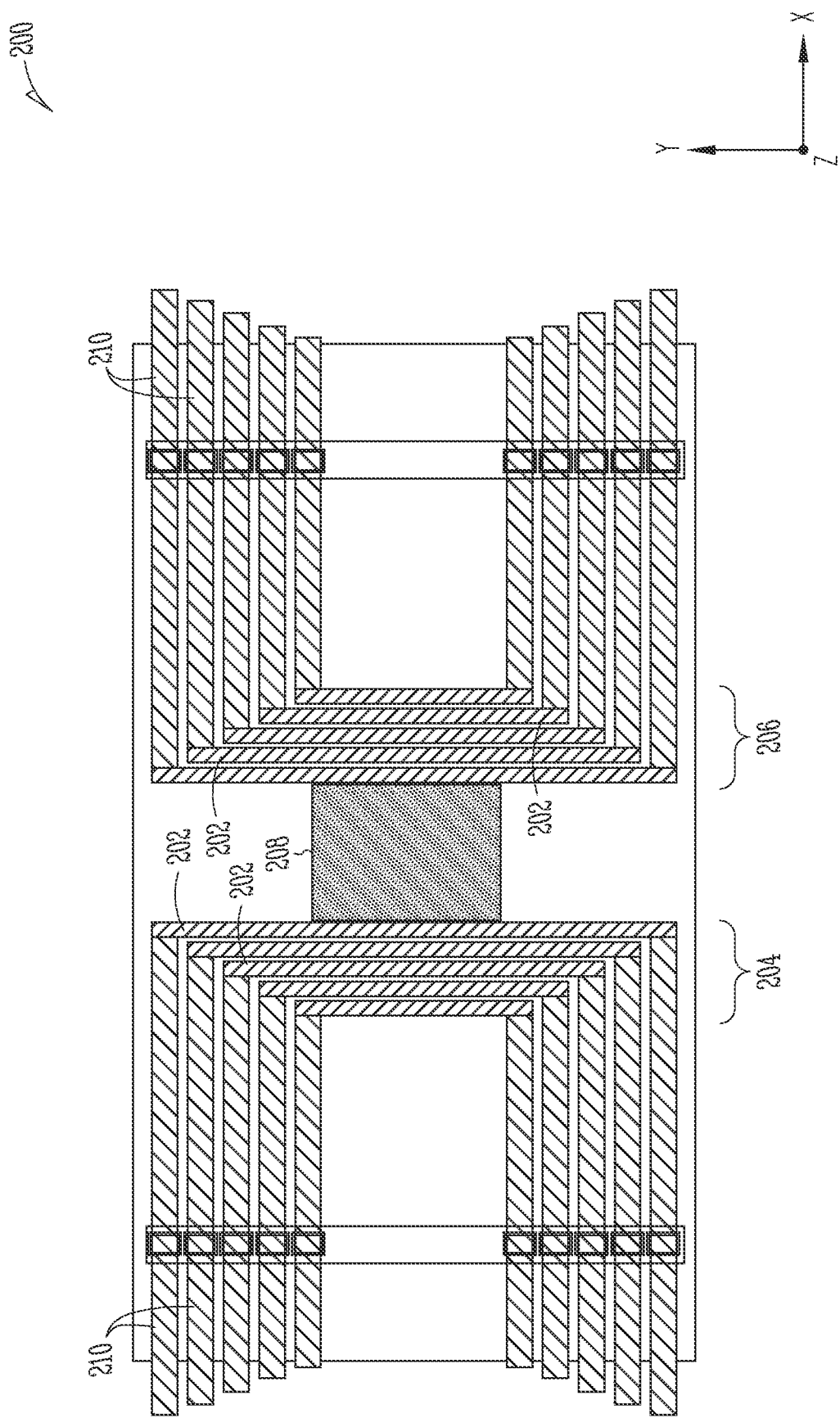
FIG. 2A depicts, in beam's eye view, an example adjustable multi-slit collimator (MSC), in accordance with one embodiment, with a fully open beam aperture.

Recent advances in radiation therapy include the development of energy-modulated radiation therapy, which allows the modulation of the particle energy of the radiation beam (e.g., the x-ray photon energy) in addition to beam shape and/or intensity. This capability can overcome the tradeoffs between high-energy radiation and low-energy radiation. High-energy radiation can achieve higher penetration and, thus, treat deeper-seated tumors, but it generally results in a substantial penumbra that limits the achievable dose gradients, risking radiation exposure of tissues adjacent the target. Using both high and low-energy radiation from different angles, penetration and dose gradients can be jointly optimized. In this context, however, conventional MLCs, which generate a usually contiguous aperture of variable width, impose limits on the efficiency with which the radiation can be delivered. For example, when using a low-energy beam to treat the edges of a target, with a conventional MLC, the dose would be delivered in two steps, one exposure for each side of the target. Similarly, conventional MLCs limit the capabilities and efficiency of microbeam therapy, which aims radiation at very small treatment targets, e.g., to irradiate complex structures.

Described herein are collimator configurations that form arrays of adjustable slits, allowing for discontiguous beam intensity patterns that, in turn, enable simultaneously exposing multiple smaller areas to radiation. Such collimators provide yet another adjustable variable for treatment planning and optimization, and can lead to greater treatment efficiency, especially in energy-modulated therapy and microbeam therapy. Herein, the contemplated collimators are referred to as "multi-slit collimators (MSCs)."

In general, an adjustable MSC device in accordance herewith includes at least one set of collimator leaves arranged in a one-dimensional array, along with a mechanism for moving the collimator leaves. Each leaf is individually movable such that the set of leaves collectively forms slits of variable width between pairs of adjacent collimator leaves. The mechanism for moving the leaves may include, e.g., pistons attached to the set of collimator leaves, which may be actuated, for instance, by indexed motors.

The collimator leaves generally extend in a direction perpendicular to the one-dimensional array (or "substantially perpendicular," allowing for some slight variations as explained below). In use, the MSC is placed such that the individual leaves extend along the beam of radiation, and the one-dimensional array is formed along a direction transverse to the beam, allowing the intensity of the transmitted beam to be varied along that transverse direction via adjustments of the spacings between the leaves. In some embodiments, the leaves further extend along a second direction transverse to the beam, perpendicular to the first, to create a one-dimensional intensity distribution of the beam. In other embodiments, multiple sets of collimator leaves, each set arranged one-dimensionally along the first direction transverse to the beam, are stacked along the second transverse direction (perpendicular to the first) to create a two-dimensional intensity distribution. Alternatively, in some embodiments, multiple sets of collimator leaves arranged along different respective transverse directions are stacked in the direction of the beam to form differently oriented sets of apertures at different positions along the beam. An MSC can also be combined with a conventional MLC placed at a different position along the beam.

In some embodiments, to account for the radiation beam divergence, the collimator leaves extend along radii emanating from a common center point, and the MSC is placed, in use, such that that center point coincides with the source of the beam (e.g., in x-ray therapy, the x-ray converter target); in other words, the MSC leaves extend in a radial direction along the beam. This means that, if the leaves are arrayed along a straight line, the orientation of the leaves slightly varies along the array and as the leaves move, and only a leaf at the beam axis extends in a direction perpendicular to the direction of the array, whereas the radially extending leaves placed to either side of the beam axis extend in a direction that deviates from the direction perpendicular to the array by a small angle, equal to the angle between the respective ray of radiation and the beam axis; the leaves are, in this case, said to extend merely "substantially perpendicularly" to the direction of the array. In some embodiments, the leaves are oriented to extend in the radial direction by means of pairs of pistons attached to each collimator leaf that move in a coordinated manner. In some embodiments, the one-dimensional array extends along an arc, in use of the MSC centered at the radiation source, and the collimator leaves are movable along arcs parallel to the array. Further, in some embodiments, the collimator leaves are wedge-shaped along the radial direction to match the beam divergence.

In various embodiments, the MSC device serves not only to generate a variable intensity distribution across the beam, but also to simultaneously provide quality assurance of the beam by measuring various beam properties, such as the overall intensity and proper functioning of the leaves. For purposes of such measurements, electrical voltages may be applied between pairs of adjacent leaves, and the electrical currents resulting from photoelectrons created by radiation hitting the leaves be measured. For example, every other leaf in a one-dimensional array of leaves may be electrically grounded, with positive voltages applied to the intervening leaves, and the combined currents from both adjacent leaves may be measured at each leaf or a subset of the leaves (e.g., each grounded leaf). By comparing the current measurements against a baseline, deviations from normal or intended operation can be detected.

The foregoing will be more readily understood from the following description of the various accompanying drawings.

For comparison with MSCs, FIG. 1 schematically illustrates a conventional MLC 100 in a beam's eye view, that is, in a plane transverse to the beam axis, or general direction of propagation of the radiation. The MLC includes two sets 102, 104 of collimator leaves 106, to the left and right of the beam. Within each set 102, 104, the leaves 106 are arrayed along a first transverse (as shown, vertical) direction, with each leaf 106 extending and movable along a second transverse (as shown, horizontal) direction. The leaves 106 can be individually moved in and out of the beam, allowing the transverse beam profile 108 to be shaped. The MLC 100 is suitable for generating a single aperture of variable boundary, but very limited in its ability to create multiple slits (with any slit being formed between two rows of a pair of fully closed collimator leaves having a width in the first direction that is an integer multiple of the leaf width in the first direction).

FIGS. 2A-2D illustrate an adjustable MSC 200 in accordance with one embodiment. With reference FIG. 2A, which depicts the MSC 200 in beam's eye view, this collimator includes an array of leaves 202, e.g., grouped into two banks 204, 206 of leaves 202 to the left and right of the axis of the beam 208 (only some of the leaves 202 being labeled to avoid obfuscation of the drawing). The leaves are made of a material suitable to block radiation, e.g., without limitation, a metal like tungsten. The leaves 202 are arrayed along and individually moveable in a first direction in a plane transverse to the beam 208, and they extend in a second transverse direction perpendicular to the first. For example, as shown, the leaves 202 are arranged in a horizontal array (along x) and extend vertically (along y). The vertical extent of the beam 208 is limited, in this example, by a rectangular aperture that precedes the MSC 200 in the direction of beam propagation, and the individual leaves 202 each extend at least far enough to fully cover the beam 208 vertically. The MSC 200 further includes pistons 210 attached to the leaves 202 and extending from the leaves 202 horizontally. Via these pistons 210, the leaves 202 can be moved in the horizontal direction (x), allowing for continuous adjustments of the width of the slits formed between pairs of adjacent leaves 202. As shown, the pistons 210 may include sets of pistons 210 attached at the top and bottom of each leaf 202, which aids in smooth and stable motion. To facilitate attachments at different positions along the beam axis subject to spatial constraints, the leaves 202 may differ in vertical extent (length along y), as shown. The pistons 210 may be made, e.g., of metal, or generally of any material that is chemically resistant to the radiation (in that it does not easily break down when hit by the beam 208).

Figure 2B:
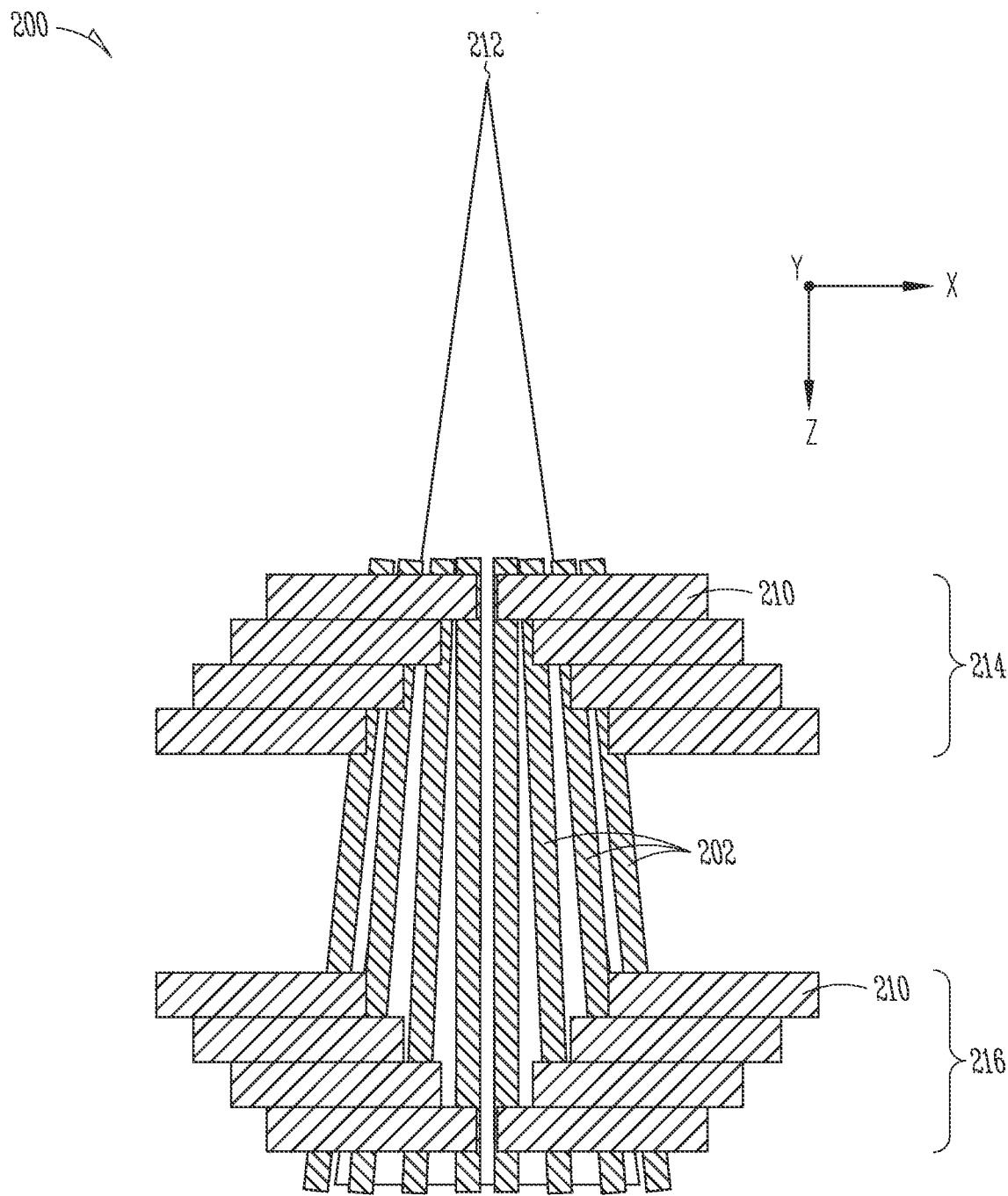
FIG. 2B depicts the example adjustable MSC of FIG. 2A in overhead view, illustrating the leaf configuration and orientation relative to a radiation source.

FIG. 2B depicts the example adjustable MSC 200 of FIG. 2A in overhead view, illustrating the leaf configuration and orientation relative to a radiation source. As shown, the leaves may fan out from a symmetry center 212 at the location of the radiation source, that is, they may extend radially in the general direction of the beam, to match the beam divergence. The horizontal (x) position of each leaf 202 may be controlled independently of the other leaves by the associated set of (horizontal) pistons 210. As can be seen, the set of pistons 210 may include pistons attached not only at the top and bottom of each leaf 202, but also at two positions along the beam axis. The pistons 210 move in a coordinated fashion to maintain the conformity of the created slits to the beam divergence. For example, in general, the pistons 210 closer to the radiation source at center point 212 (collectively 214) are positioned farther in towards the beam axis than the pistons 210 farther from the radiation source (collectively 216) to orient the leaves 202 radially. Note that, although the leaves 202 are shown as uniform in thickness, they may, alternatively, be wedge-shaped (e.g., as illustrated in the context of another embodiment in FIGS. 6B-8C).

Figure 2C:
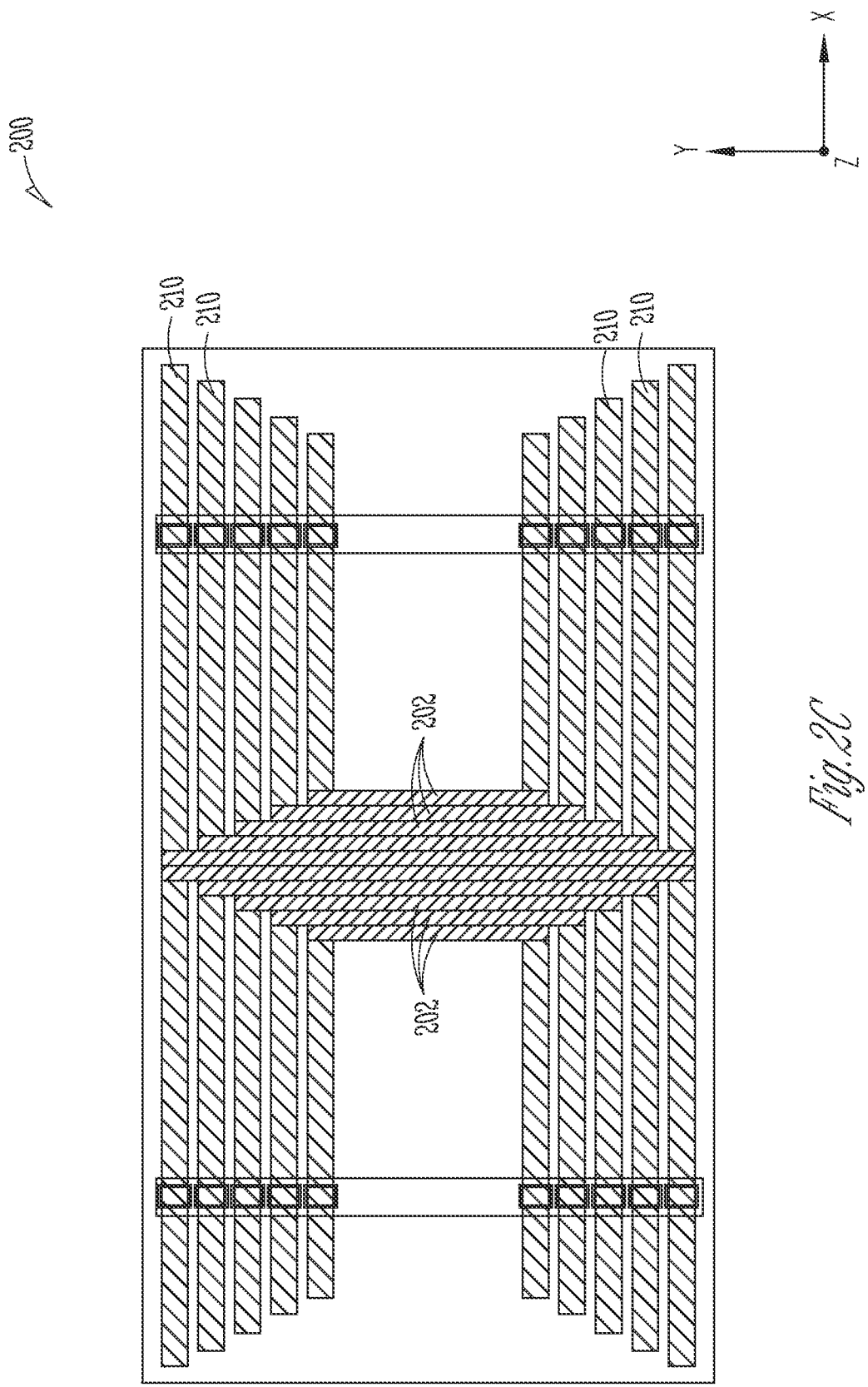
FIG. 2C depicts, in beams' eye view, the example adjustable MSC of FIG. 2A with a fully closed beam aperture.
Figure 2D:
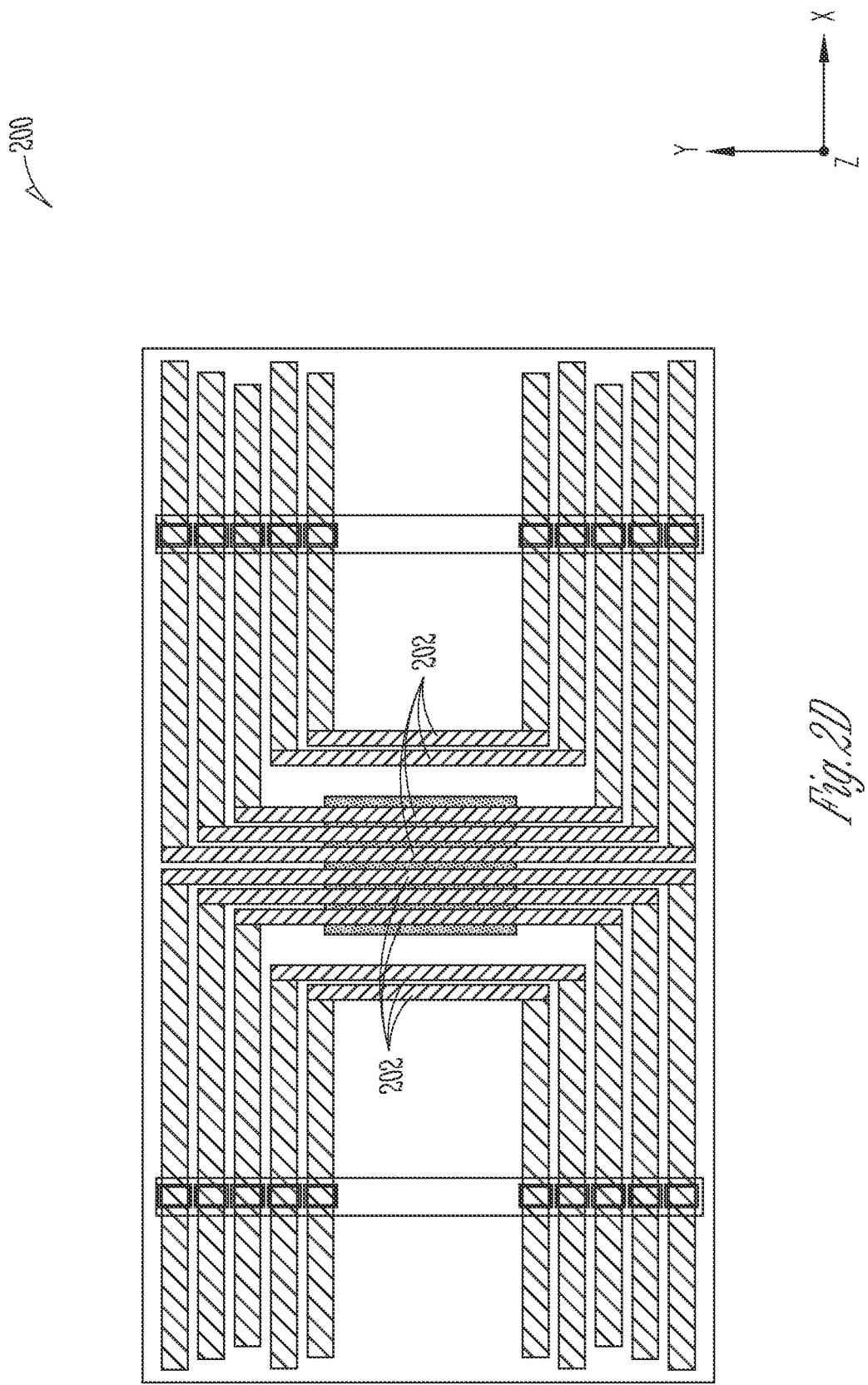
FIG. 2D depicts, in beams' eye view, the example adjustable MSC of FIG. 2A with leaf positions for a transverse beam intensity distribution composed of multiple slits of varying widths.

While FIG. 2A illustrates the MSC 200 in a configuration that creates a fully open beam aperture, FIG. 2C depicts the MSC 200, likewise in beam's eye view, with a fully closed beam aperture. FIG. 2D shows the MSC 200 with leaf positions for a transverse beam intensity distribution composed of multiple slits of varying widths.

The MSC 200 shown in FIGS. 2A-2D allows creating a one-dimensional intensity distribution. To achieve a transverse beam intensity distribution that varies in two dimensions, the MSC 200 may be used in conjunction with a second (e.g., similar or identical) MSC or a conventional MLC, placed at a different distance from the beam source.

Figure 3A:
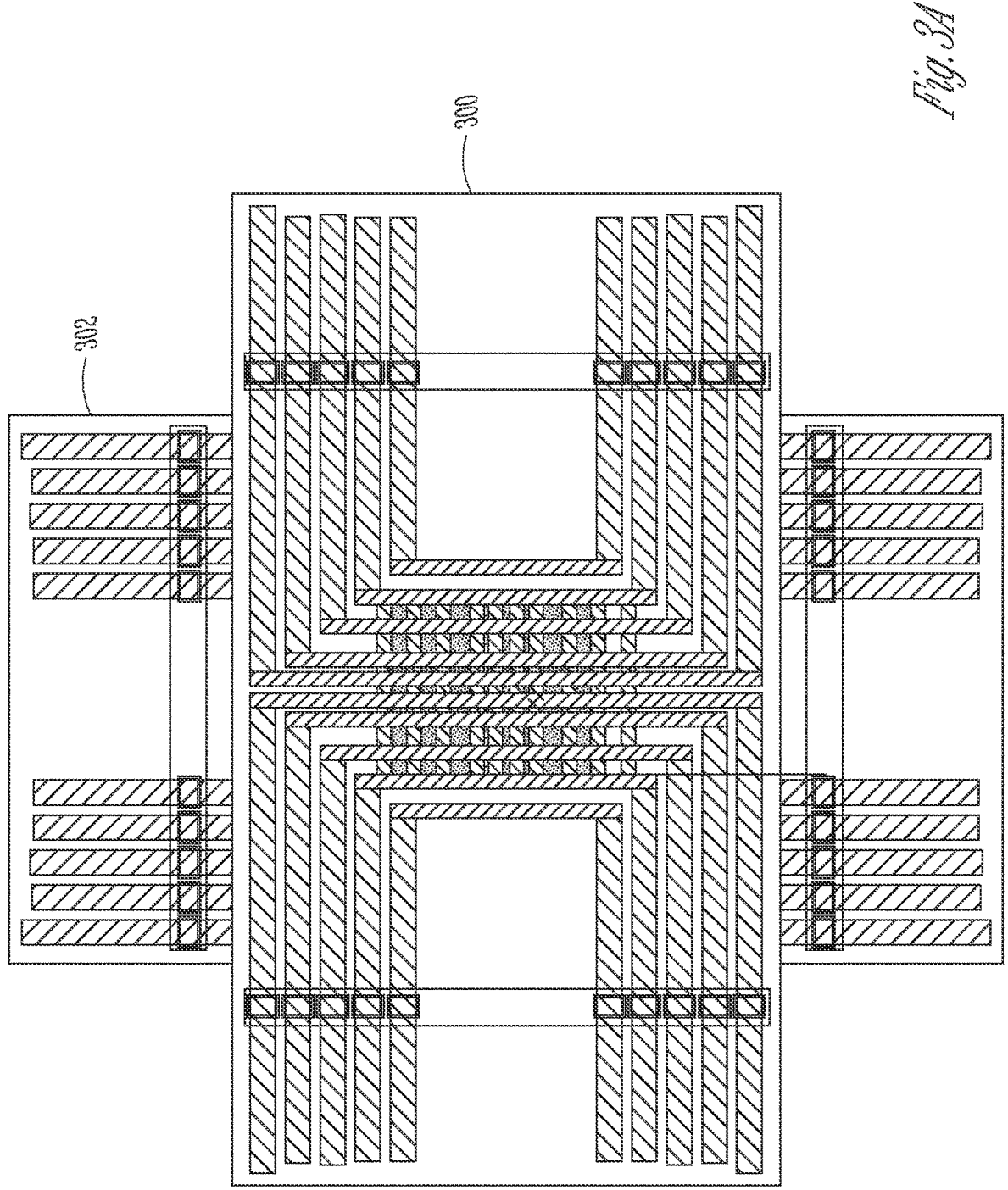
FIG. 3A depicts, in beam's eye view, an example device with two MSCs oriented perpendicular to each other, in accordance with one embodiment, to achieve a transverse beam intensity distribution that varies in two dimensions.
Figure 3B:
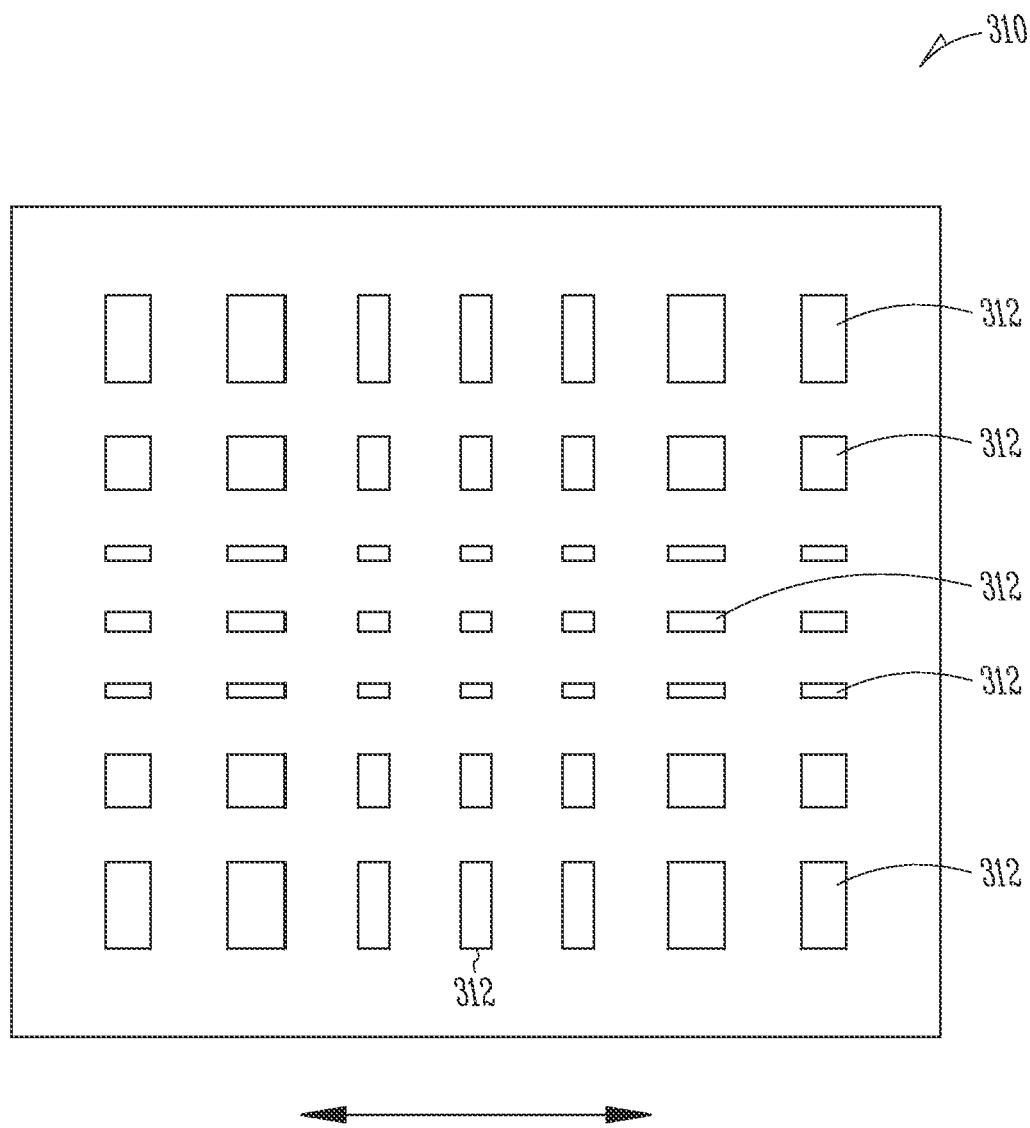
FIG. 3B depicts an example two-dimensional transverse beam intensity distribution as can be achieved with the device of FIG. 3A.

FIG. 3A depicts, in beam's eye view, an example MSC device with two MSCs 300, 302 (e.g., implemented by the MSC 200) oriented perpendicular to each other, in accordance with one embodiment, to achieve a transverse beam intensity distribution that varies in two dimensions. The two MSCs 300, 302 are "stacked" in the radial direction, such that the beam intensity is first modulated along one transverse dimension, and then independently along the other transverse dimension. For example, as shown, the beam first encounters MSC 302, which forms a set of horizontal slits, and then MSC 300, which forms a set of vertical slits. Collectively, the two MSCs 300, 302 form a set of "micro-apertures" arranged along rows and columns. FIG. 3B depicts an example two-dimensional transverse beam intensity distribution 310 as can be achieved with the device of FIG. 3A, illustrating the micro-apertures 312 (only some being labeled). As will be appreciated by those of ordinary skill in the art, the two MSCs 300, 302 need not necessarily be oriented perpendicular to one another. They may, for example, be oriented at an acute angle relative to each other to create parallelogram-shaped, instead of rectangular, micro-apertures.

Figure 4A:
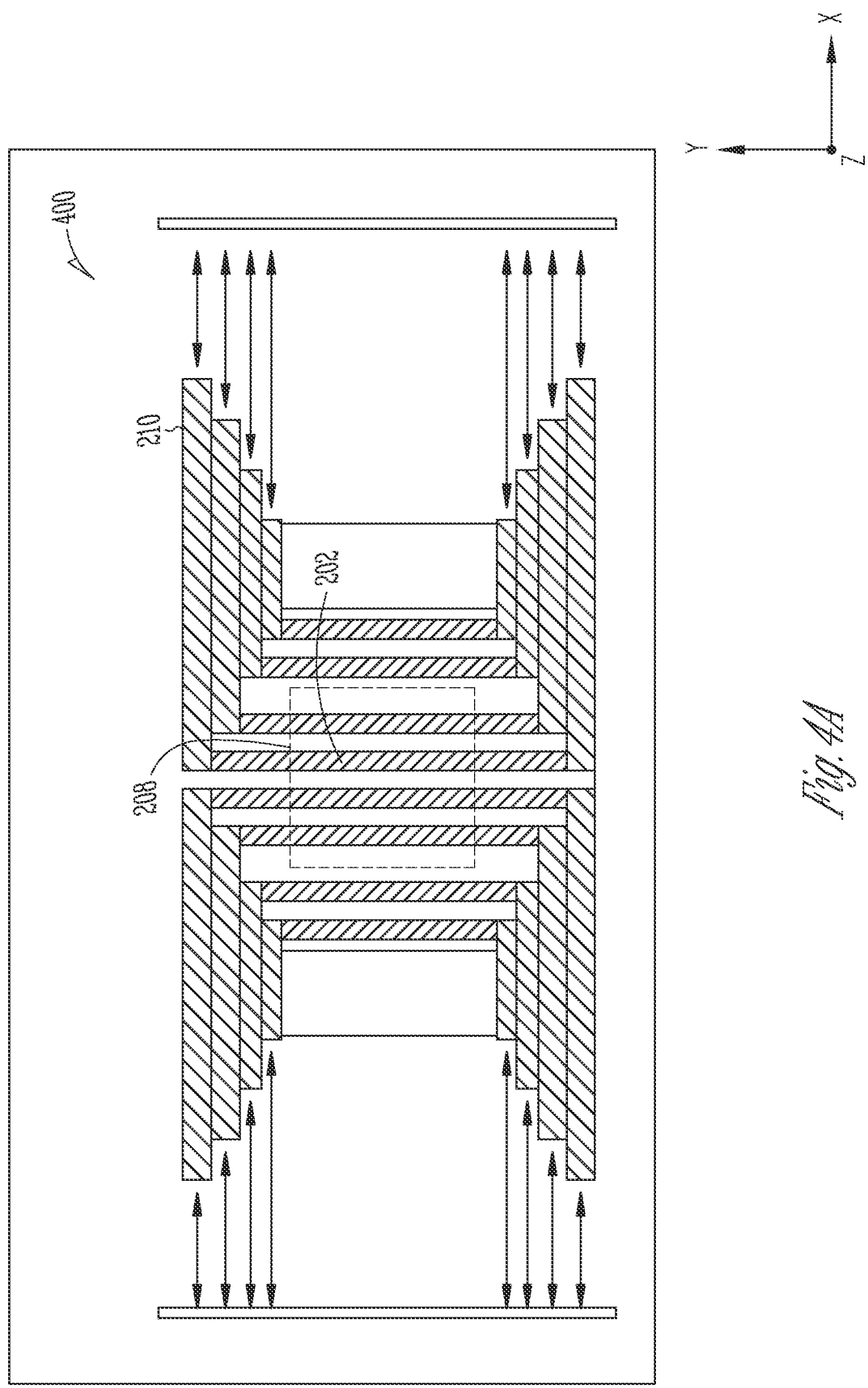
Figure 4C:
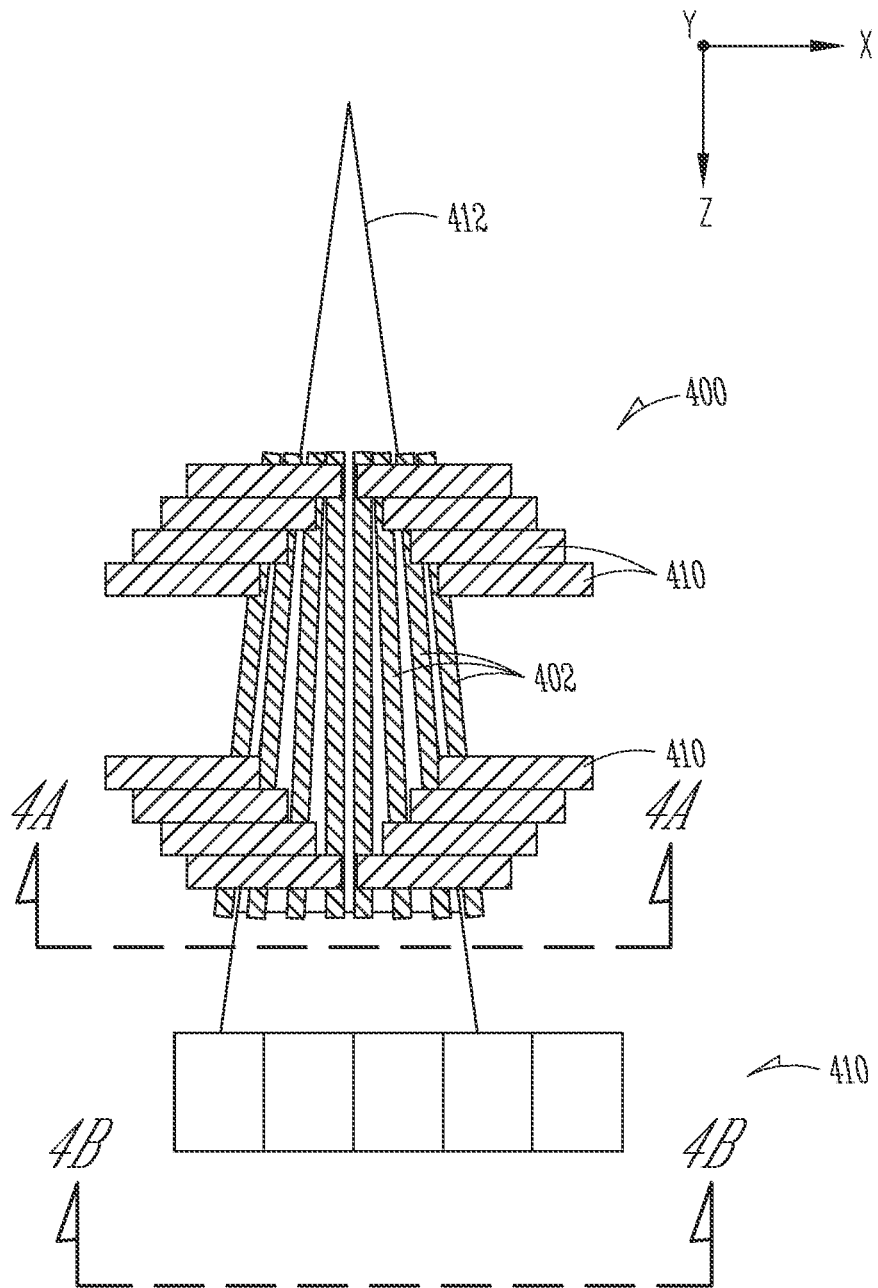
FIG. 4C depicts the MSC and MLC of FIGS. 4A and 4B in overhead view.

FIGS. 4A and 4B depict, in beam's eye view, an adjustable MSC 400 by itself and the MSC 400 in conjunction with a perpendicularly oriented conventional MLC 410, respectively, in accordance with one embodiment. FIG. 4C depicts the MSC 400 and MLC 410 in overhead view, showing their different positions along the axis of the beam 412. In this example, the beam 412 encounters first the MSC 400 and then the MLC 410. As can be seen in FIG. 4A, the horizontally arrayed, vertically extending leaves 202 of the MSC 400 form vertical slits that create a horizontal beam intensity distribution along the horizontal (x) direction (the first transverse direction), similarly to MSC 200 in FIG. 2D. The likewise horizontally arrayed, vertically oriented pairs of opposing leaves 106 of the MLC 410 are vertically movable to limit the beam aperture vertically (in the y direction, which is here the second transverse direction), with an aperture size and vertical position that vary as a function of the fixed horizontal position of each pair of leaves 106.

As will be appreciated, the MSC/MLC combination of FIGS. 4A-4B and the pair of MSCs in FIGS. 3A-3B achieve different respective types of two-dimensional intensity distributions, with different degrees of freedom in shaping each distribution. The MSC/MLC combination does not allow for multiple apertures at a given horizontal location, but it allows the vertical location of the aperture to vary depending on horizontal position. The pair of MSCs, on the other hand, allows for multiple slits (a non-contiguous aperture) both horizontally and vertically, but both the horizontal and the vertical intensity distribution exhibit translational symmetry. Whether the MSC/MLC combination or the pair of MSCs is preferable will generally depend on the particular application and associated desired transverse variation in beam intensity.

FIGS. 5A-5C illustrate the utility of an MSC, as contrasted with an MLC, in treating the periphery or edges of a target. More specifically, FIG. 5A depicts an example desired radiation dose distribution 500 relative to a spherical target 502. The dose distribution 500 features two peaks 504, 506 positioned to overlap with the edges of the target 502. FIG. 5B illustrates two steps of creating the desired dose distribution 500 with an MLC 508 used sequentially in two different transverse positions. In the depicted system configuration, the beam 510 first encounters a primary collimator with a conical aperture 512 to define the beam size, and then the leaves of the MLC 508. In the first step, the MLC 508 is positioned left of the beam axis to create the first peak 504. Thereafter, the MLC 508 is shifted to the right of the beam axis to create the second peak 506 in the second step.

FIG. 5C illustrates a two-slit configuration of an MSC 514, in accordance with one embodiment, that achieves the desired dose distribution 500 of FIG. 5A in a single step. Following the conical aperture 512, the beam encounters the MSC 514, which blocks the central portion of the beam, but leaves slits to both sides of the beam axis to simultaneously irradiate the edges of the target 502 with intensity peaks 504, 506. A single configuration of the MSC 514 characterized by two slits, thus, achieves the same purpose as the two sequential configurations of the MLC 508.

In the preceding examples, the leaves in the MSC were arranged one-dimensionally, and a two-dimensional intensity distribution, where accomplished, utilized two MSCs or an MSC and MLC at different radial positions in conjunction. It is also possible, alternatively, to arrange collimator leaves two-dimensionally in a surface transverse to the beam axis, e.g., by stacking multiple one-dimensional arrays in a transverse direction perpendicular to the direction of the one-dimensional arrays. In this case, the spatial extent of the individual beams in the second transverse direction is generally reduced as compared to one-dimensional leaf configurations, as now the multiple one-dimensional arrays of leaves together cover the transverse beam profile in both directions. The two-dimensional array may be planar, or curved, e.g., to match the diverging beam.

FIG. 6A depicts, in beam's eye view, an example two-dimensional arrangement 600 of collimator leaves 602 of an adjustable MSC in accordance with one embodiment. As shown, the collimator leaves 602 may form a two-dimensional array comprising multiple (e.g., as shown, five) vertical columns of one-dimensional radial MSCs, stacked in the horizontal (x) direction. In the depicted example, as can be seen in FIG. 6C, the columns alternate between five and six leaves 602 per column (columns 604, 606, respectively). Note that the orientation of the MSC in the transverse plane is arbitrary; the collimator may be rotated such that, alternatively, the two-dimensional array is formed of multiple rows of radial collimator leaves 602 stacked in the vertical direction.

FIGS. 6B and 6C are cross-sectional views of the arrangement 600 of collimator leaves 602 along two planes through columns 604, 606 with five and six leaves 602, respectively, illustrating the configuration and orientation of the leaves 602 relative to the radiation source 610 in accordance with one embodiment. As can be seen, the leaves 602 all extend radially along portions of radii emanating from the radiation source at 610, and the one-dimensional arrangement of leaves 602 within each column is along a circular arc (rather than a straight line). Further, as can be seen, the collimator leaves 602 in this radial MSC configuration are wedge-shaped, with adjustable, likewise wedge-shaped gaps (or slits) between pairs of adjacent leaves 602 within each column. Along the radial direction, the leaf thickness varies between a smaller thickness (which may be substantially zero, corresponding to a sharp tip) at the end closer to the radiation source 610 to a greater thickness at the end farther from the radiation source 610; FIG. 6B shows two enlarged cross-sectional views 612, 614 of one pair of collimator leaves 602 at locations closer to and farther away from the source 610, respectively. The depicted thickness, which increases with radial distance from the source 610, is in the y-direction within the y-z-plane, that is, the plane of each one-dimensional arrangement (or column). Additionally, the leaves may be wedge-shaped, and increase in thickness towards larger radial distances from the source 610, in the x direction, that is, the direction in which the one-dimensional leaf arrangements are stacked.

Figure 7:
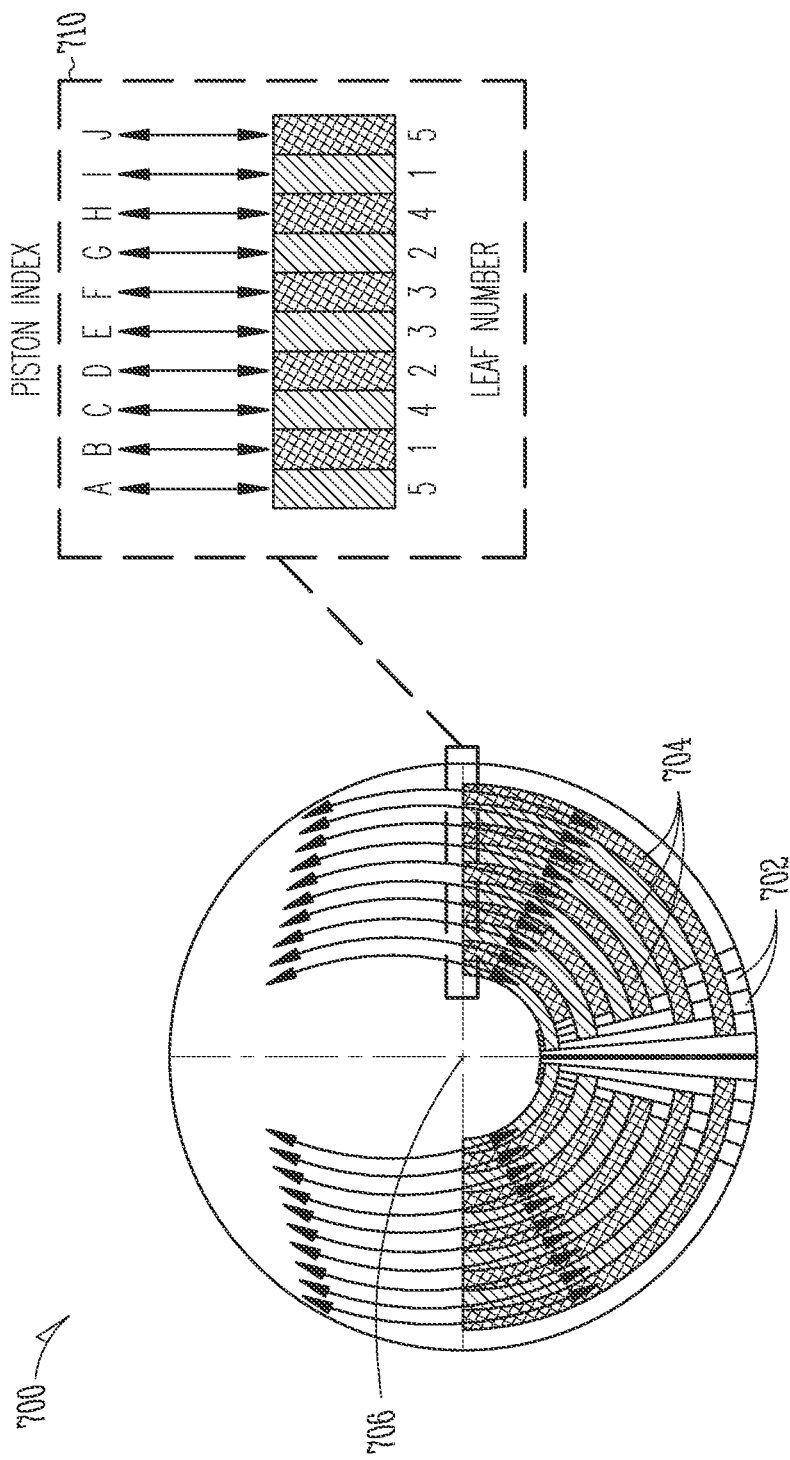
FIG. 7 depicts an example MSC with a radial arrangement of collimator leaves, in accordance with one embodiment, in overhead view, illustrating a mechanism for moving the leaves.

FIG. 7 depicts an example MSC 700 with a radial arrangement of collimator leaves (e.g., as depicted in FIGS. 6B-6C), in accordance with one embodiment, in overhead view, illustrating a mechanism for moving the leaves. As in the MSCs 200, 300, the wedge-shaped leaves 702 can be moved by pistons 704 that extend perpendicularly from the leaves at different radial positions away from the location 706 of the radiation source. The leaves 702 are movable in an angular direction about the radiation source by the pistons 704, which are themselves curved and extend and move along arcs that are concentric with the array of leaves 702. While, in principle, only one piston 704 is needed for each leaf, two pistons, attached to two points closer to and farther from the radiation source, that move in unison may be used for greater stability and accuracy in controlling the leaf positions. The wedge shape of the leaves 702 in conjunction with the angular motion ensures inherently that the created slits match the beam aperture.

The insert 710 illustrates an example configuration of attachment points between pistons 704 and leaves 702. The ten pistons 704 on each side are indexed by A to J from largest to smallest radius; the leaves 702 are labeled by 1-5 from the periphery to the center of the one-dimensional array. For example, pistons with indexes A and J are attached to leaf 5, pistons with indexes B and I are attach to leaf 1, and so on; in general, in this example configuration, pairs of pistons 704 attached to the same leaf 702 are "nested." Other piston arrangements are, of course, also possible; the depicted configuration is merely one non-limiting example.

Note that, if multiple circular one-dimensional arrays of radially extending collimator leaves 702 are stacked, in a direction transverse to the beam and perpendicular to the one-dimensional arrays, associated sets of pistons 704 may likewise be stacked. Such stacking may result in a cylindrical arrangement, where the two-dimensional array of collimator leaves 702 extends along part of the curved surface of a cylinder whose axis goes through the location 706 of the radiation source. More complex piston arrangements or alternative mechanisms for moving the individual leaves 702 may allow instead for a spherical configuration, with the array of collimator leaves 702 extending along a surface portion of a sphere centered at the location 706 of the radiation source.

Figure 8A:
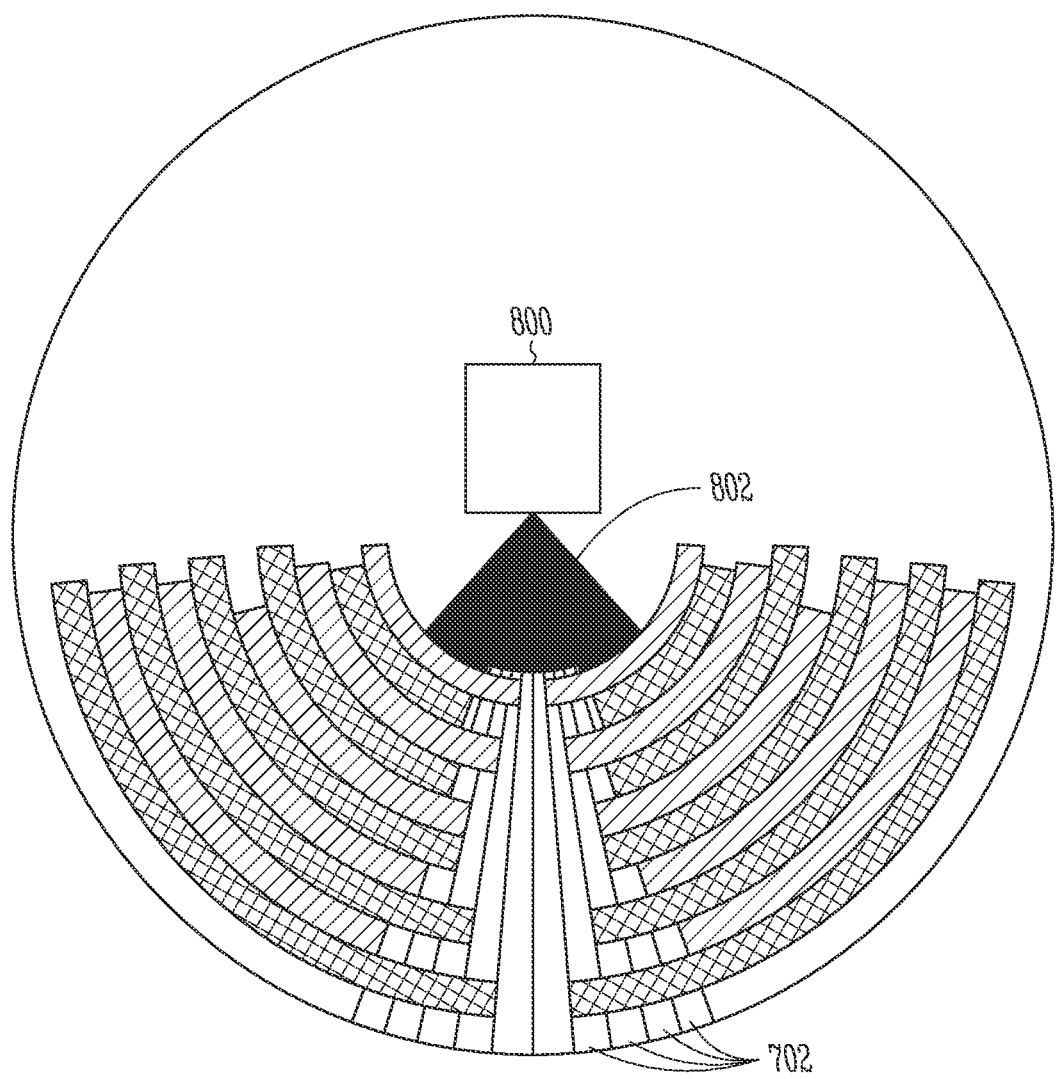
FIGS. 8A-8C depict the MSC of FIG. 7 with a fully closed beam aperture, a fully open beam aperture, and a partially open beam aperture, respectively.
Figure 8B:
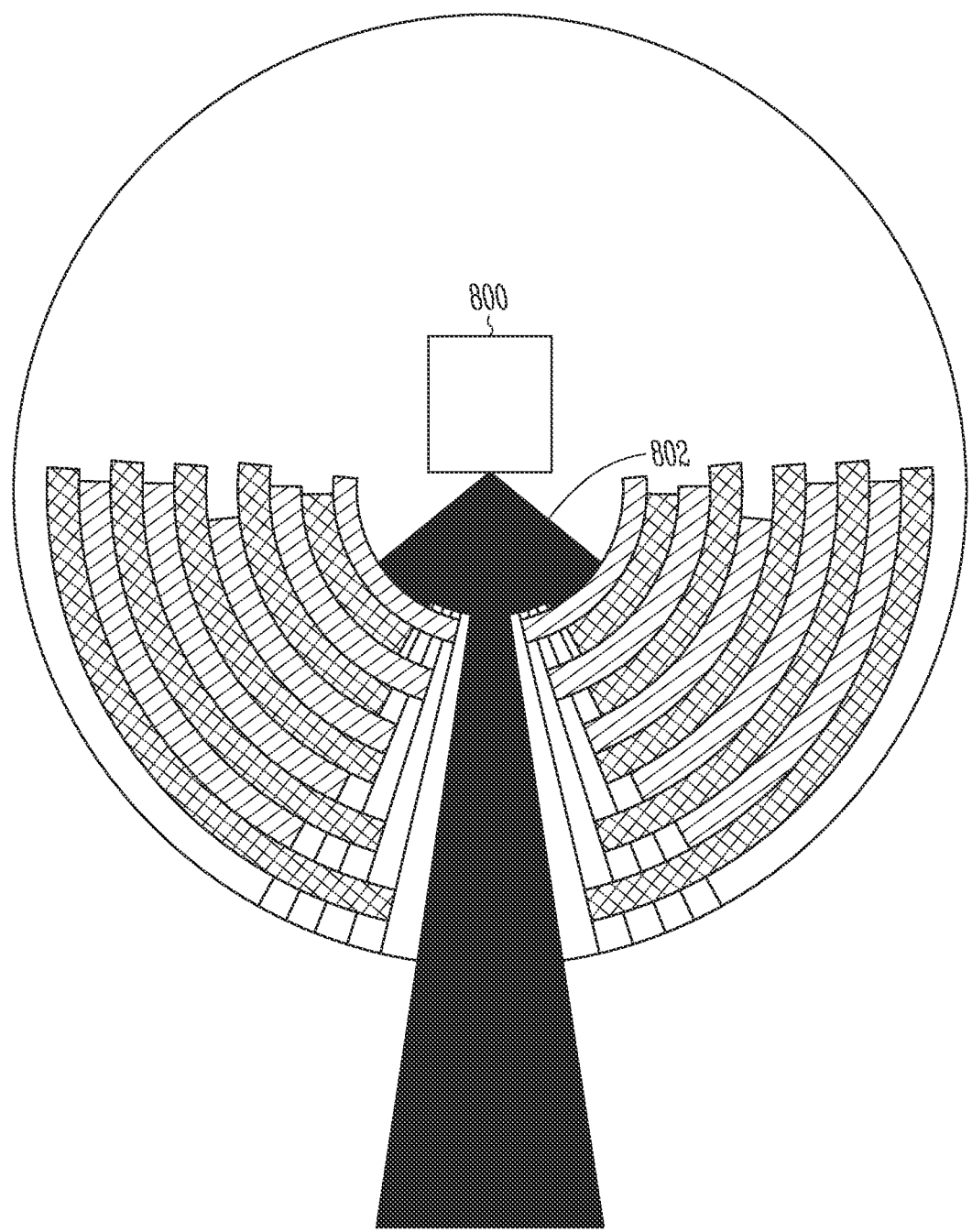
Figure 8C:
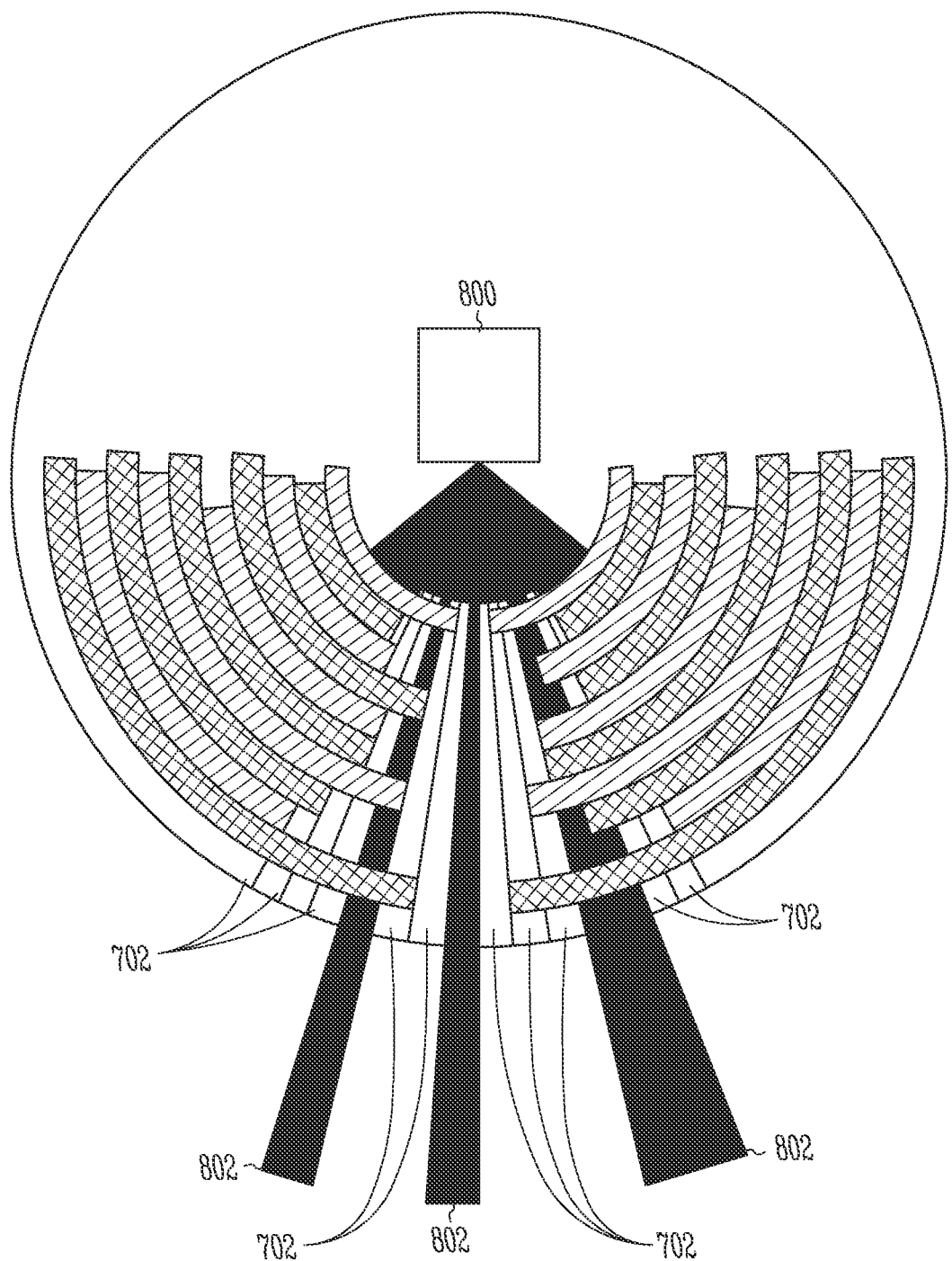

FIGS. 8A-8C depict the MSC 700 of FIG. 7 with a fully closed beam aperture, a fully open beam aperture, and a partially open beam aperture, respectively. The various leaf arrangements are shown relative to the radiation source 800, and the resulting beam 802 is indicated. When the leaves 702 are at their fully closed positions, the beam 802 is fully blocked as shown in FIG. 8A. When the leaves 702 are removed as far from the beam axis as possible, a central beam 802 (laterally confined due to the contiguous central aperture formed by the MSC 700) is transmitted, as shown in FIG. 8B. When the leaves 702 are spaced apart along the circumference of the radial arrangement, a multi-slit beam field is formed.

Figure 9:
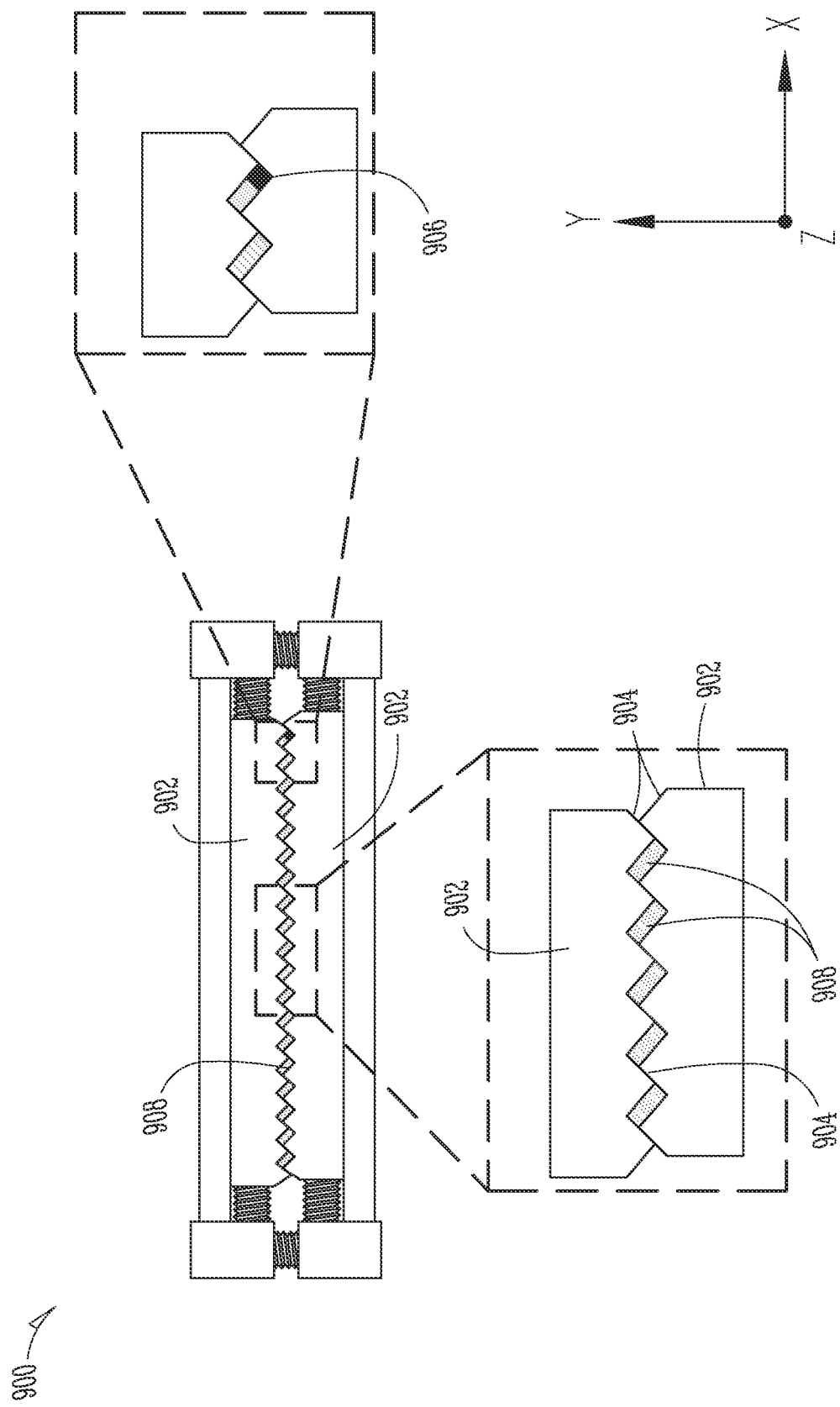
FIG. 9 depicts, in beam's eye view, an example MSC, in accordance with one embodiment, with a regular slit pattern of adjustable size.

FIG. 9 depicts, in beam's eye view, an example MSC 900, in accordance with one embodiment, with a regular slit pattern of adjustable size. This collimator 900 includes a pair of plates 902 from which two respective rows of regularly arranged interlocking triangular teeth 904 extend. Alignment pins 906 inserted between the opposing rows of teeth 904 keep the two plates 902 at a small distance, creating a regular arrangement of slits 908 that are oriented along the edges of the teeth 904. The alignment pins 906 may be selected from a kit including pins of various cross-sectional sizes to accommodate various respective slit widths.

Figure 10A:
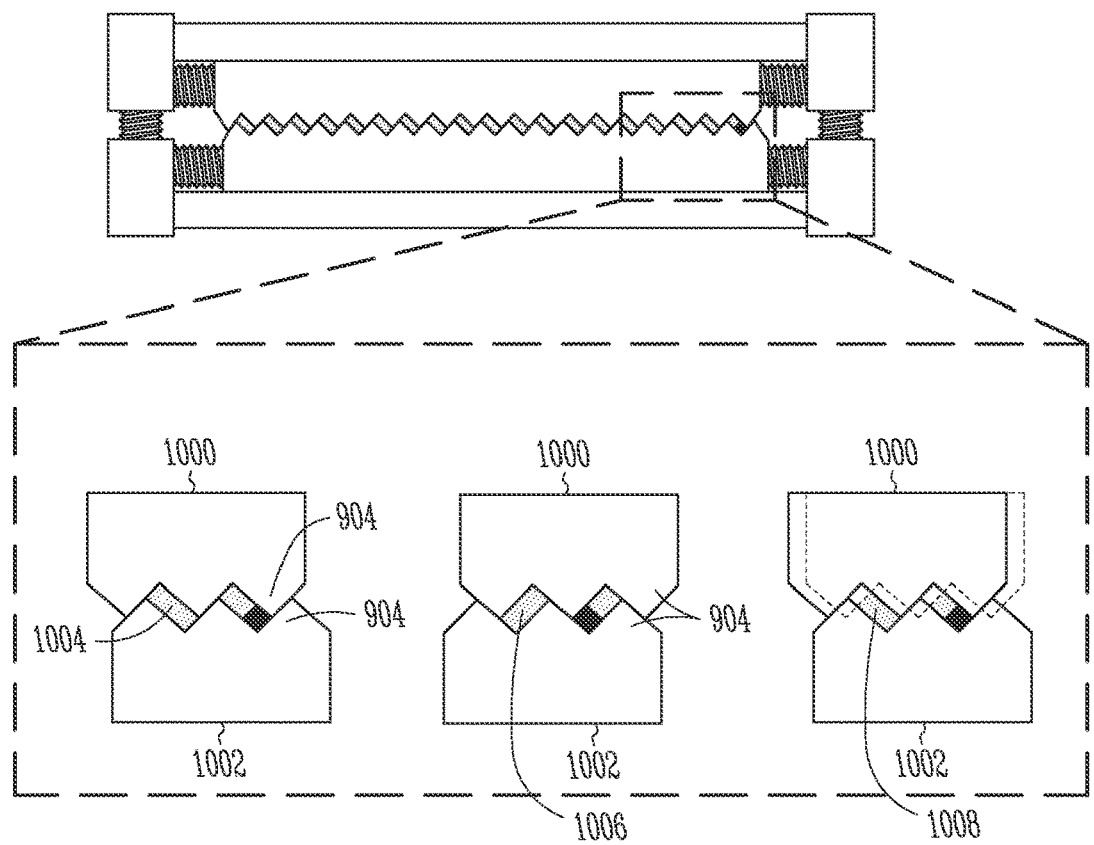
FIGS. 10A and 10B illustrate, in beam's eye view, a slit pattern created, in accordance with one embodiment, by multiple layers of MSCs as shown in FIG. 9.
Figure 10B:
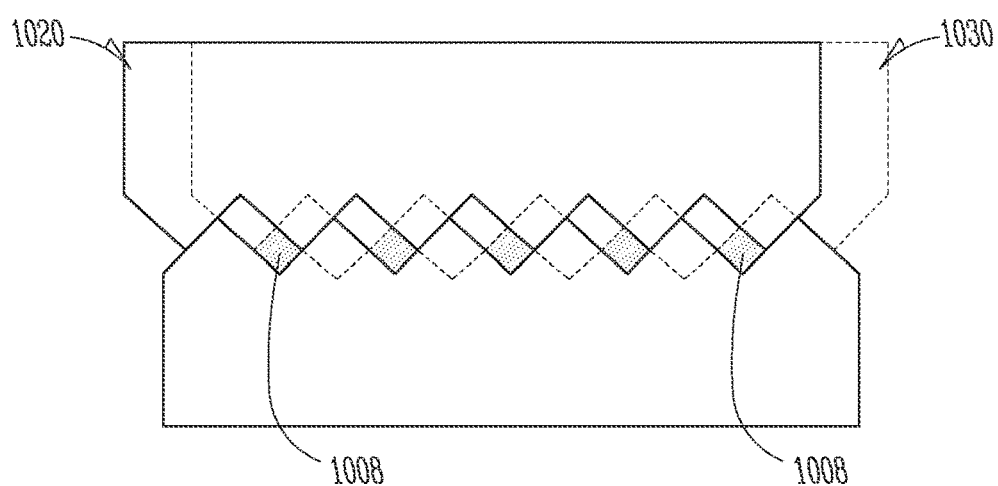

FIGS. 10A and 10B illustrate, in beam's eye view, a slit pattern created, in accordance with one embodiment, by multiple layers of MSCs 900 as shown in FIG. 9. As illustrated in FIG. 10A, the slits formed between the teeth 904 are oriented in either of two principal directions, depending on the relative horizontal position of the upper collimator plate 1000 to the lower collimator plate 1002. If the teeth 904 of the upper plate 1000 contact the left edges of the teeth 904 of the lower plate 1002, the resulting slits 1004 are slanted to the left; if the teeth 904 of the upper plate 1000 contact the right edges of the teeth 904 of the lower plate, the slits 1006 are slanted to the right. As shown in FIG. 10B, two collimators 900 (labeled 1020 and 1030, respectively) can be stacked in the direction of the beam (z) to create overlapping sets of slits 1004, 1006 oriented in different directions, and thereby to form micro-apertures 1008 that are even smaller than an individual slit.

Figure 11:
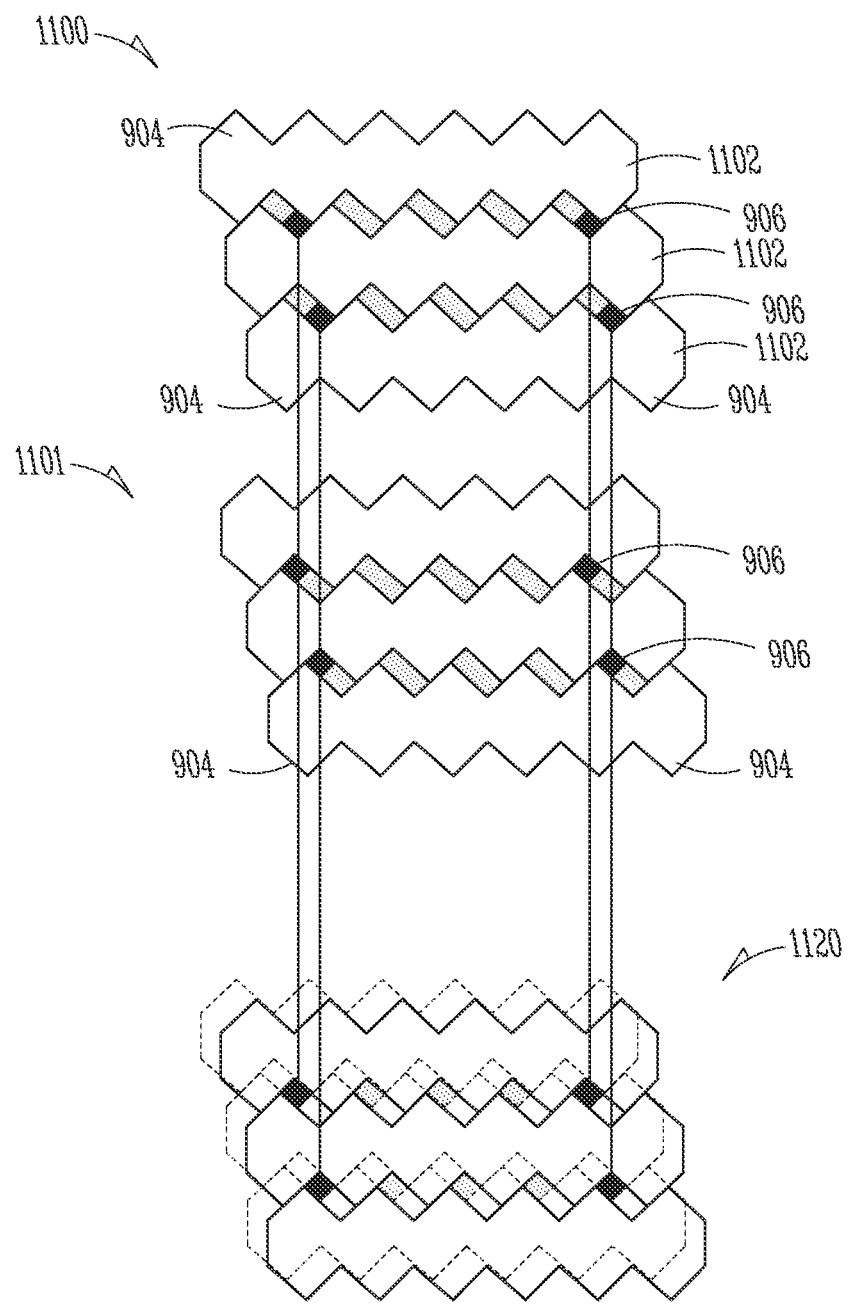
FIG. 11 illustrates how MSCs that create two-dimensional regular slit patterns can be combined to achieve a regular microbeam pattern, in accordance with one embodiment.

FIG. 11 illustrates how MSCs 1100, 1101 that create two-dimensional regular slit patterns can be combined to achieve a regular microbeam pattern, in accordance with one embodiment. To form a two-dimensional array of slits, the MSC 900 may be extended in the direction perpendicular to the row of teeth, e.g., by stacking multiple pairs of horizontal collimator plates 1102 vertically (or multiple pairs of vertical collimator plates horizontally). As depicted, the individual plates 1102 may, in this case, have rows of teeth 904 both at the bottom and at the top to each simultaneously form part of two pairs of plates (except for the top-most and bottom-most plate, which are each part of only one pair of plates). Collectively, n plates stacked in this manner create a two-dimensional pattern of slits including n−1 rows. For example, a slit pattern with two rows is formed with the three plates 1102 shown. Slit orientation and size can, as in FIGS. 10A-10B, be selected via the placement and choice of the pins 906.

As further illustrated, multiple such two-dimensional MSCs 1100, 1101 can be stacked in the direction of the beam, in different transverse positions and/or with different alignments between opposing rows of teeth, to reduce the size of the resulting micro-apertures of the combined beams. FIG. 11 depicts two such layers 1100, 1101 in beam's eye view. The layers 1100, 1101 are aligned with each other along the pins 906, as indicated by vertical lines, creating the micro-aperture pattern 1120.

The collimator arrangements of FIGS. 9-11 may find application, e.g., in microbeam therapy, where a regular pattern of small, high-intensity beams separated by low-intensity intervals is used, in lieu of a broader uniform beam of moderate intensity, to treat a given target. Beneficially, these collimators are simple and robust, due to their static nature (that is, the lack of moving parts in operation). The embodiments of FIGS. 2A-8C, on the other hand, provide greater flexibility in modulating the intensity distribution across the beam profile, and may be used in applications that require irregular intensity distributions.

Figure 12:
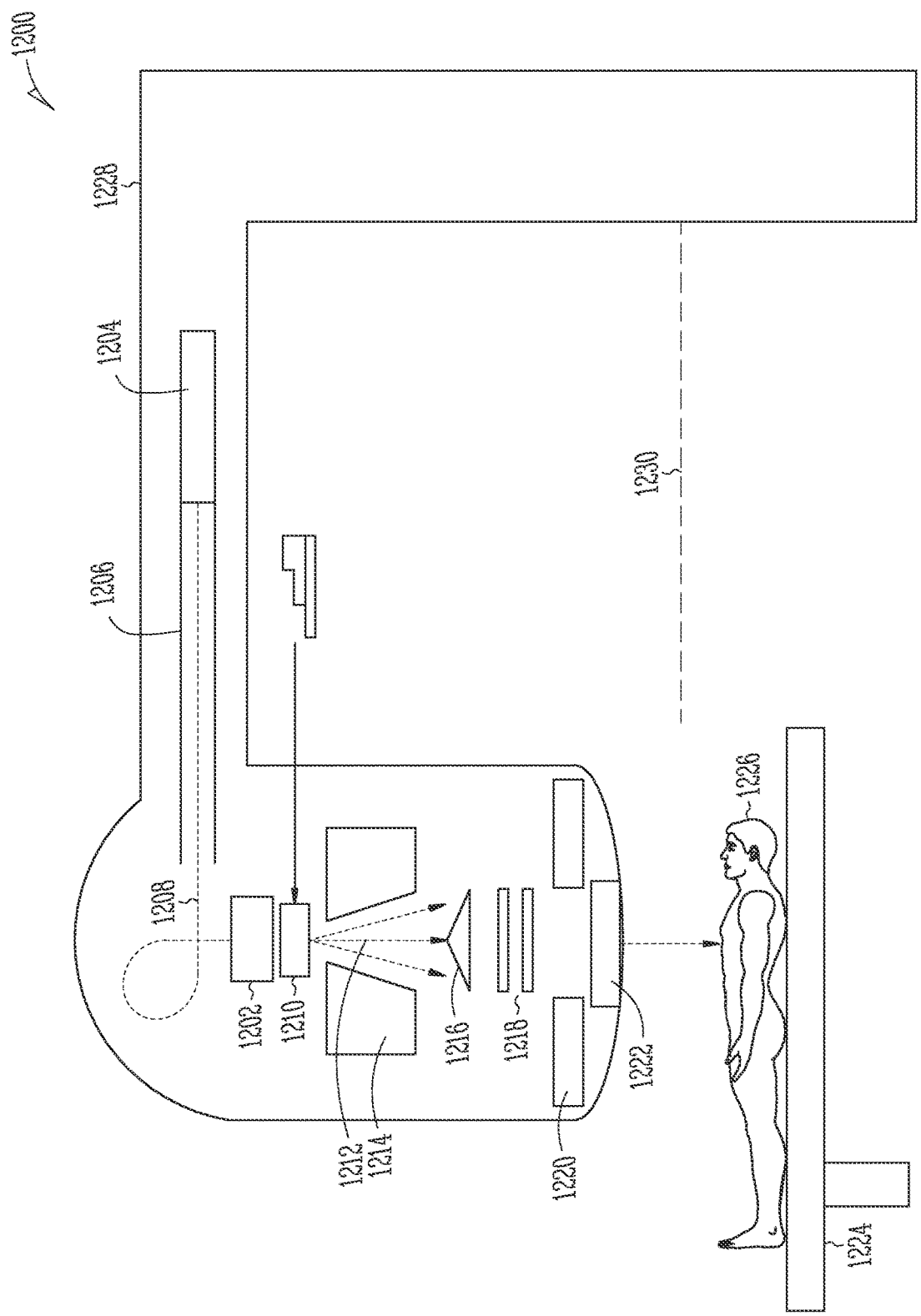
FIG. 12 schematically illustrates an example x-ray radiotherapy system in which MSCs as described herein may be employed.

FIG. 12 schematically illustrates an example x-ray radiotherapy system 1200 in which MSCs as described herein may be employed. The system 1200 includes a medical LINAC, e.g., as known to those of ordinary skill in the art, optionally retrofitted with an electron-energy modulator (conceptually indicated at 1202) upstream of the x-ray converter target 1210 or, alternatively, with a combined energy-modulating x-ray converter target in place of a conventional x-ray converter target. The LINAC includes an electron gun 1204 or other electron injection system, and an accelerator that includes an accelerator waveguide 1206 and is driven by a radio-frequency (RF) power source (not shown), in which the electrons are accelerated to MeV energies. When the electrons hit a target of suitable material, they generate, in the course of being slowed down by interactions with the target atoms, x-rays 1212 (primarily Bremsstrahlung); the target 1210 is therefore also referred to as the x-ray converter target. The generated x-rays 1212 have a broad spectral energy distribution with photon energies up to and including the energy of the incident electrons, and with a mean energy (also referred to as the "effective energy" of the x-ray photons) amounting to about one third of that maximum energy. In accordance with various embodiments, the spectral energy distribution of the x-ray beam 1212 may be modified by controllably reducing the energy of the electron beam 1208 with an add-on electron-energy modulator 1202 (or an energy-modulating layer of an integrated energy-modulating x-ray converter target module 1202/1210) located somewhere in the path of the electron beam. Using such electron-energy modulation, a LINAC ordinarily producing, e.g., 6 MV x-ray beams can generate lower-energy x-rays, e.g., x-rays characterized by spectral energy distributions with maximum energies less than 4 MeV, or less than 1 MeV in some embodiments. This capability enables creating dose distributions with sharp penumbras.

The LINAC further includes an x-ray beam collimation and monitoring system, which may, e.g., include a primary collimator 1214 that defines a maximum circular field of the x-ray beam, a flattening filter 1216 for generating a uniform intensity distribution over the collimated field, a monitoring chamber (e.g., an ionization chamber) for measuring the photon (and any remaining electron) output and x-ray beam flatness, and a secondary collimator 1220 for generating, e.g., a rectangular field. To provide control over the intensity distribution of the beam, the LINAC is further equipped, in accordance herewith, with one or more MSCs 1222, optionally in conjunction with a conventional MLC. In some embodiments, the MSC(s) 1222, (optionally along with certain upstream components) are configured to rotate about the beam axis, allowing the transverse beam profile to assume various orientations relative to the treatment target. As described below with respect to FIG. 13, the MSC(s) 1222 may also serve, in addition to or in lieu of the monitoring chamber, to provide quality assurance of the beam, e.g., to monitor the intensity distribution and spectral energy of the x-ray beam.

The radiotherapy system 1200 may further include a treatment table (or treatment couch) 1224, on which a patient 1226 may be positioned for x-ray treatment. LINAC components including at least the x-ray converter target 1210 and x-ray beam collimation and monitoring system downstream thereof (collectively the "x-ray source") may be mounted in a gantry 1228 that can rotate about a (horizontal) gantry axis 1230 to irradiate the treatment target in the patient 1226 from different angles. In some embodiments, a full 360° rotation is possible. The gantry 1228 may also allow tilting the x-ray beam (e.g., via independent movement of a treatment head housing the x-ray source) relative to the vertical direction, and/or laterally moving the beam parallel to the gantry axis 1230. Alternatively or additionally, the treatment table 1224 may be configured to move linearly or rotate underneath the x-ray source. The radiotherapy system 1200 further includes a control system (not shown) for controlling the operation of the LINAC, including, in particular, the MSCs 1222 and, if applicable, the electron-energy modulator 1202, for intensity-modulated and/or energy-modulated therapy. The control system may execute a treatment plan, e.g., computed based on image data (e.g., computerized axial tomography (CAT) scans or magnetic resonance imaging (MRI) data) of a region within the patient that includes the treatment target, to adjust the spectral energy and beam intensity/shape/fluence distribution as the x-ray beam 1212 is moved around the treatment target. The control system may be implemented by a suitably programmed computer or, generally, any suitable combination of hardware and/or software.

Figure 13:
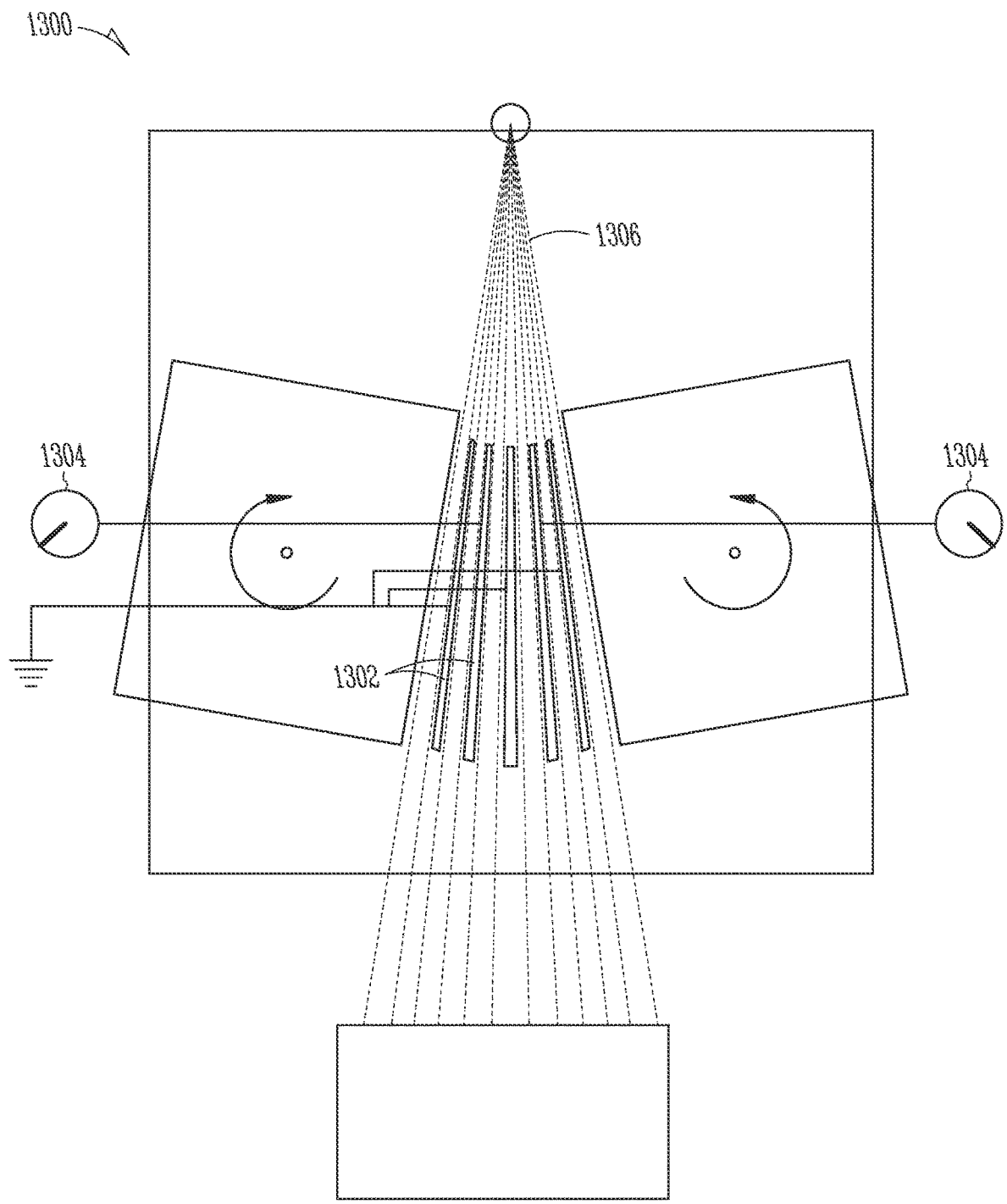
FIG. 13 is an overhead view of a radial MSC, illustrating use of the MSC for beam monitoring in accordance with various embodiments.

FIG. 13 is an overhead view of a radial MSC 1300 (e.g., as illustrated in FIGS. 6A-6C), illustrating use of the MSC for beam monitoring in accordance with various embodiments. Here, the collimator leaves 1302 are electrically conductive (e.g., made of a metal such as tungsten) and form part of electrical circuits, with every other leaf having a voltage of several hundred volts, and leaves in between being electrically grounded. The x-rays 1306 that strike the collimator leaves 1302 free electrons via the photoelectric effect, and these electrons can flow across the apertures from one leaf to its two neighboring leaves (e.g., from a grounded leaf to two neighboring leaves held at positive electrical potential). The leaves 1302 may be electrically connected to devices that measures small electrical currents, such as electrometers 1304, to collect the resulting electrical currents at the leaves (only two such electrometers being shown). In this manner, each pair of adjacent slits, or apertures, between leaves 1302 forms an individual detector akin to an ionization chamber. The strength of the measured signal (e.g., the electrical current level) is generally dependent on the volume of cavity between the leaves 1302, the energy of the x-rays 1306 striking the leaves 1302, and the beam intensity. Collectively, the detectors associated with the individual leaves provide for the spatially resolved measurement of these beam-characterizing parameters.

FIGS. 14A-14D illustrate example detector response curves obtained with an MSC 1300 as shown in FIG. 13, in accordance with various embodiments. Each response curve is created from the current signals measured at multiple detectors associated with respective MSC leaves, plotted from detector 1-$n$ as a bar diagram (the response curve obtained by connecting the bars for the individual detectors). In the example, n=7. FIG. 14A depicts a baseline response curve 1400, as may be obtained during calibration for a particular MSC configuration. From the shape of a response curve subsequently acquired for the same MSC configuration, as compared with the baseline response curve 1400, various x-ray delivery characteristics can be determined. A mechanical defect in the MSC (which becomes more likely with smaller apertures) may be reflected in an abnormal curvature of the response curve 1402, as shown in FIG. 14B. A response curve 1404 similar in shape to the baseline response curve 1400, but shifted in magnitude, as shown in FIG. 14C, may indicate a change in the beam intensity. A sharper response curve 1406, as shown in FIG. 14D, may be an indication of increased spectral energy. Thus, the shape of the response curve can provide valuable information about the cause of a deviation from the baseline response curve 1400. During treatment, as the target MSC configuration and target values of the beam spectral energy and/or beam intensity are changed (e.g., while the beam is moved around the target), response curves may be acquired continuously, and each curve may be compared against a baseline curve measured for the same target beam parameters (e.g., the same MSC configuration, same spectral energy and intensity as desired, etc.); the baseline curves may be stored in a calibration library of such curves. The detector response of the MSC 1300 may be connected to safety interlocks to terminate operation of the system if the response curve deviates beyond a tolerance margin from the relevant baseline curve.

Although embodiments have been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings show by way of illustration, and not limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This description, therefore, is not to be taken in a limiting sense, and the scope of various embodiments is defined only by the appended claims, along with the full range of equivalents to which such claims are entitled.

What is claimed is:

1. An adjustable multi-slit collimator device comprising:
   a set of three or more collimator leaves arranged in a first one-dimensional array along a first direction and individually movable along the first direction to form slits of variable width between pairs of adjacent collimator leaves; and
   a mechanism for moving the collimator leaves.

2. The device of claim 1, wherein the collimator leaves extend in a radial direction substantially perpendicular to the first direction.

3. The device of claim 2, wherein the collimator leaves are wedge-shaped along the radial direction.

4. The device of claim 3, wherein the collimator leaves further extend in a second direction that is perpendicular to the first direction and substantially perpendicular to the radial direction.

5. The device of claim 3, further comprising:
   one or more additional sets of collimator leaves each arranged in a respective additional one-dimensional array extending parallel to the first one-dimensional array along the first direction, the one or more additional sets of collimator leaves being stacked with the set of collimator leaves in a second direction that is perpendicular to the first direction and substantially perpendicular to the radial direction.

6. The device of claim 1, wherein the mechanism comprises pistons attached to the set of collimator leaves.

7. The device of claim 6, wherein the first one-dimensional array extends along an arc and the first direction is an angular direction, and wherein the pistons extend, and the collimator leaves are movable, in the first direction along arcs parallel to the first one-dimensional array.

8. The device of claim 6, wherein the pistons extend in a direction parallel to the first one-dimensional array.

9. The device of claim 8, wherein pairs of pistons attached to a same collimator leaf are movable in a coordinated manner to orient the collimator leaves in a radial direction substantially perpendicular to the first one-dimensional array.

10. The device of claim 6, wherein the pistons are movable by electronically controlled actuators.

11. The device of claim 1, further comprising:
    a second set of collimator leaves arranged in a second one-dimensional array extending in a second direction perpendicular to the first direction, the first and second sets being stacked in a direction perpendicular to the first and second directions.

12. The device of claim 1, further comprising:
    a second set of collimator leaves, comprising pairs of collimator leaves movable in a direction perpendicular to the first direction and forming gaps of variable size in the direction perpendicular to the first direction, the pairs arranged in a second one-dimensional array along the first direction, the first and second one-dimensional arrays being stacked in a direction perpendicular to both the first direction and the direction in which the collimator leaves of the second set are movable.

13. The device of claim 1, wherein the collimator leaves are electrically connected to two alternating electrical potentials along the first one-dimensional array, the device further comprising detectors for measuring electrical currents generated at the leaves.

14. A radiotherapy system, comprising:
a radiation source configured to emit a beam of radiation towards a target; and
placed in the beam between the radiation source and the target, an adjustable multi-slit collimator device comprising one or more sets of three or more collimator leaves, the three or more collimator leaves within each set arranged in a one-dimensional array along a first direction that is generally perpendicular to a direction of the beam, the collimator leaves within each set being individually movable along the first direction to form slits of variable width between pairs of adjacent collimator leaves to thereby modify a transverse intensity distribution of the beam.

15. The radiotherapy system of claim 14, further comprising a gantry for moving the radiation source along with the multi-slit collimator device about the target.

16. The radiotherapy system of claim 15, further comprising a control system configured to control the multi-slit collimator device in synchronization with the gantry.

17. The radiotherapy system of claim 16, further comprising an energy modulator configured to modify a spectral energy of the radiation, the control system further configured to control the energy modulator in synchronization with the gantry.

18. The radiotherapy system of claim 14, wherein the multi-slit collimator is further configured as a beam monitoring device measuring electrical currents across apertures between the collimator leaves, the system further comprising a control system configured to determine parameters of the beam based on the electrical currents measured across the apertures.

19. A method for modulating an intensity distribution of a beam of radiation, the method comprising:
using an adjustable multi-slit collimator device placed in the beam and comprising a set of three or more collimator leaves that are arranged in a one-dimensional array along a first direction substantially perpendicular to a direction of the beam and that are individually movable along the first direction, operating actuators associated with the collimator leaves to position the collimator leaves to create a pattern of two or more slits between the collimator leaves based on a target intensity distribution.

20. The method of claim 19, further comprising operating the actuators to conform orientations of the collimator leaves to a divergence of the beam.

* * * * *